(12) United States Patent
Shiku et al.

(10) Patent No.: US 11,497,768 B2
(45) Date of Patent: Nov. 15, 2022

(54) ANTIGEN-BINDING PROTEIN THAT RECOGNIZES MAGE-A4-DERIVED PEPTIDE

(71) Applicant: MIE UNIVERSITY, Tsu (JP)

(72) Inventors: Hiroshi Shiku, Tsu (JP); Yasushi Akahori, Tsu (JP); Yuya Kato, Tsu (JP); Yoshihiro Miyahara, Tsu (JP)

(73) Assignee: MIE UNIVERSITY, Tsu (JP)

( * ) Notice: Subject to any disclaimer, the term of this patent is extended or adjusted under 35 U.S.C. 154(b) by 379 days.

(21) Appl. No.: 16/619,212

(22) PCT Filed: Jun. 5, 2018

(86) PCT No.: PCT/JP2018/021561
§ 371 (c)(1),
(2) Date: Dec. 4, 2019

(87) PCT Pub. No.: WO2018/225732
PCT Pub. Date: Dec. 13, 2018

(65) Prior Publication Data
US 2020/0276237 A1 Sep. 3, 2020

(30) Foreign Application Priority Data
Jun. 5, 2017 (JP) .............................. JP2017-111157

(51) Int. Cl.
| | | |
|---|---|---|
| A61K 35/17 | (2015.01) | |
| C07K 14/725 | (2006.01) | |
| C07K 14/705 | (2006.01) | |
| C07K 16/28 | (2006.01) | |
| C12N 15/63 | (2006.01) | |
| A61K 39/00 | (2006.01) | |

(52) U.S. Cl.
CPC .......... *A61K 35/17* (2013.01); *C07K 14/7051* (2013.01); *C07K 14/70521* (2013.01); *C07K 14/70578* (2013.01); *C07K 16/2833* (2013.01); *C12N 15/63* (2013.01); *A61K 2039/505* (2013.01); *C07K 2317/24* (2013.01); *C07K 2317/54* (2013.01); *C07K 2317/55* (2013.01); *C07K 2317/56* (2013.01); *C07K 2317/622* (2013.01)

(58) Field of Classification Search
CPC .............. A61K 35/17; A61K 2039/505; C07K 14/7051; C07K 14/70521; C07K 14/70578; C07K 16/2833; C07K 2317/24; C07K 2317/54; C07K 2317/55; C07K 2317/56; C07K 2317/622; C12N 15/63
See application file for complete search history.

(56) References Cited

U.S. PATENT DOCUMENTS

| 2014/0242701 A1 | 8/2014 | Shiku et al. |
| 2014/0322344 A1 | 10/2014 | Shiku et al. |
| 2016/0367651 A1 | 12/2016 | Shiku et al. |
| 2018/0148503 A1 | 5/2018 | Scheinberg et al. |
| 2018/0177816 A1 | 6/2018 | Shiku et al. |
| 2019/0111078 A1 | 4/2019 | Shiku et al. |
| 2021/0137977 A1 | 5/2021 | Chaudhary |

FOREIGN PATENT DOCUMENTS

| WO | 2013051718 A1 | 4/2013 | |
| WO | 2016191246 A2 | 12/2016 | |
| WO | WO-2016199141 A2 * | 12/2016 | .............. A61P 35/00 |
| WO | 2019232503 A1 | 12/2019 | |

OTHER PUBLICATIONS

Rabia et al Understanding and overcoming trade-offs between antibody affinity,specificity, stability and solubility (Biochemical Engineering Journal 137 (2018) 365-374) (Year: 2018).*
SEQ ALignments (ABSS) SEQ ID No. 36 . Hartnett (Year: 2022).*
SEQ ALignments (ABSS) SEQ ID No. 38. Hartnett (Year: 2022).*
J. Barrett, "Expanding the Antigenic Repertoire Of CAR-T Cells with "TCR-Like" Antibody Specificity", Cytotherapy, Aug. 2016, vol. 18, No. 8, pp. 929-930.
R.J. Brentjens, et al: "Safety and persistence of adoptively transferred autologous CD19-targeted T cells in patients with relapsed or chemotherapy refractory B-leukemias", Blood, Nov. 2011, vol. 118, No. 18, pp. 4817-4828.
M.-T. Duffour, et al., "A MAGE-A4 Peptide Presented by HLA-A2 Is Recognized by Cytolytic T Lymphocytes", European Journal of Immunology, 1999, vol. 29, pp. 3329-3337.
English translation of the International Search Report dated Aug. 28, 2018 for parent application No. PCT/JP2018/021561.
English translation of the Written Opinion dated Aug. 28, 2018 for parent application No. PCT/JP2018/021561.
R.C. Hillig, et al, "High-Resolution Structure of HLA-A*0201 in Complex With A Tumour-Specific Antigenic Peptide Encoded by the MAGE-A4 Gene", Journal of Molecular Biology, 2001, vol. 310, pp. 1167-1176.
N. Kyogoku, et al., "Time-Dependent Transition of the Immunoglobulin G Subclass and Immunoglobulin E Response in Cancer Patients Vaccinated with Cholesteryl Pullulan-Melanoma Antigen Gene-A4 Nanogel", Oncology Letters, Dec. 2016; vol. 12; Issue No. 6; pp. 4493-4504.
M. Qing, et al, "A Novel TCR-Like CAR with Specificity for PR1/HLA-A2 Effectively Targets Myeloid Leukemia in Vitro when Expressed in Human Adult Peripheral Blood and Cord Blood T Cells", Cytotherapy, 2016, vol. 18, Issue 8; pp. 985-994.
M.V. Maus, et al, "Targeting Intracellular Antigens Using Chimeric Antigen Receptors", Molecular Therapy, May 2012, vol. 20, Supplement 1, p. S206.

(Continued)

*Primary Examiner* — Amy E Juedes
*Assistant Examiner* — Brian Hartnett
(74) *Attorney, Agent, or Firm* — J-Tek Law PLLC; Jeffrey D. Tekanic; Scott T. Wakeman

(57) ABSTRACT

CAR-T cells for cancer therapy are provided with an antibody that recognizes the MAGE-A4-derived-peptide/HLA-A2 complex. The antibody includes the VH amino acid sequence of SEQ ID NO: 36 and the VL amino acid sequence of SEQ ID NO: 38. The antibody preferably is provided with the amino acid sequence of SEQ ID NO: 32. Such CAR-T cells can be used in CAR infusion therapy in which a cancer-specific intracellular antigen is used.

20 Claims, 19 Drawing Sheets

Specification includes a Sequence Listing.

(56) References Cited

OTHER PUBLICATIONS

D. Muraoka, et al, "Nanogel-Based Immunologically Stealth Vaccine Targets Macrophages in the Medulla of Lymph Node and Induces Potent Antitumor Immunity", American Chemical Society, ACS Nano, Sep. 2014, vol. 8, No. 9, pp. 9209-9218.

T. Nakagawa, et al, "Development of Next-Generation Adoptive Immunotherapy Using Cytotoxic T-Lymphocyte (CTL) Expressing Chimeric Antigen-Receptor(CAR)", Drug Delivery System, 2013, vol. 28, Issue No. 1; pp. 35-44.

T. Dao, et al, "Targeting the Intracellular WT1 Oncogene Product with a Therapeutic Human Antibody", Science Translational Medicine, Mar. 2013, vol. 5, Issue 176, 176ra133, pp. 1-11.

P. Van Der Bruggen, et al, "Tumor-Specific Shared Antigenic Peptides Recognized by Human T Cells", Immunological Reviews, 2002, vol. 188, pp. 51-64.

A. Yasushi, et al.; "Development of TCR-like scFv CAR that Recognizes MAGE-A4230-239/HLA-A*02:01 Complex", Abstracts of the 76th Annual Meeting of the Japanese Cancer Association, Dec. 31, 2017; vol. 109, Issue 1, p. 102; J-1036.

G. Zhang, et al, "Anti-Melanoma Activity of T Cells Redirected with a TCR-Like Chimeric Antigen Receptor", Scientific Reports, 2014; vol. 4, article No. 3571 , pp. 1-8.

"Clinical Safety and Preliminary Efficacy of MAGE-A4 TCR Gene-Modified T Cells to Treat Malignant Tumors"—Full Text View—ClinicalTrials.gov, Sep. 27, 2012, XP055737560, Retrieved from the Internet by the EPO at URL: https://clinicaltrials.gov/ct2/show/NCT01694472?term=mage-a4&draw=1 &rank=1[retrieved on Oct. 7, 2020].

Miyahara Y., et al., "A novel CAR-T therapy targeting MAGE-A4p230-239/HLAA* 02:01 complex for solid tumours", Conference Abstract, 25th Anniversary Congress of the European Society of Gene and Cell Therapy, Oct. 18-20, 2017, vol. 28, No. 12, p. A36, ISSN: 1557-7422.

Office Action dated Apr. 19, 2022, in related JP application No. 2019-523909, and machine translation thereof.

Supplementary European Search Report dated Feb. 2, 2021, in related EP application No. 18 813 904.2, including Search Report, Search Opinion and examined claims 1-13.

* cited by examiner

CAR zG

SEQUENCE LISTING

```
<160> NUMBER OF SEQ ID NOS: 38

<210> SEQ ID NO 1
<211> LENGTH: 10
<212> TYPE: PRT
<213> ORGANISM: Homo sapiens

<400> SEQUENCE: 1

Gly Val Tyr Asp Gly Arg Glu His Thr Val
1               5                   10

<210> SEQ ID NO 2
<211> LENGTH: 10
<212> TYPE: PRT
<213> ORGANISM: Artificial
<220> FEATURE:
<223> OTHER INFORMATION: 1A

<400> SEQUENCE: 2

Ala Val Tyr Asp Gly Arg Glu His Thr Val
1               5                   10
```

```
<210> SEQ ID NO 3
<211> LENGTH: 10
<212> TYPE: PRT
<213> ORGANISM: Artificial
<220> FEATURE:
<223> OTHER INFORMATION: 2A

<400> SEQUENCE: 3

Gly Ala Tyr Asp Gly Arg Glu His Thr Val
1               5                   10

<210> SEQ ID NO 4
<211> LENGTH: 10
<212> TYPE: PRT
<213> ORGANISM: Artificial
<220> FEATURE:
<223> OTHER INFORMATION: 3A

<400> SEQUENCE: 4

Gly Val Ala Asp Gly Arg Glu His Thr Val
1               5                   10

<210> SEQ ID NO 5
<211> LENGTH: 10
<212> TYPE: PRT
<213> ORGANISM: Artificial
<220> FEATURE:
<223> OTHER INFORMATION: 4A

<400> SEQUENCE: 5

Gly Val Tyr Ala Gly Arg Glu His Thr Val
1               5                   10

<210> SEQ ID NO 6
<211> LENGTH: 10
<212> TYPE: PRT
<213> ORGANISM: Artificial
<220> FEATURE:
<223> OTHER INFORMATION: 5A

<400> SEQUENCE: 6

Gly Val Tyr Asp Ala Arg Glu His Thr Val
1               5                   10

<210> SEQ ID NO 7
<211> LENGTH: 10
<212> TYPE: PRT
<213> ORGANISM: Artificial
<220> FEATURE:
<223> OTHER INFORMATION: 6A

<400> SEQUENCE: 7

Gly Val Tyr Asp Gly Ala Glu His Thr Val
1               5                   10

<210> SEQ ID NO 8
<211> LENGTH: 10
<212> TYPE: PRT
<213> ORGANISM: Artificial
<220> FEATURE:
<223> OTHER INFORMATION: 7A

<400> SEQUENCE: 8

Gly Val Tyr Asp Gly Arg Ala His Thr Val
1               5                   10
```

```
<210> SEQ ID NO 9
<211> LENGTH: 10
<212> TYPE: PRT
<213> ORGANISM: Artificial
<220> FEATURE:
<223> OTHER INFORMATION: 8A

<400> SEQUENCE: 9

Gly Val Tyr Asp Gly Arg Glu Ala Thr Val
1               5                   10

<210> SEQ ID NO 10
<211> LENGTH: 10
<212> TYPE: PRT
<213> ORGANISM: Artificial
<220> FEATURE:
<223> OTHER INFORMATION: 9A

<400> SEQUENCE: 10

Gly Val Tyr Asp Gly Arg Glu His Ala Val
1               5                   10

<210> SEQ ID NO 11
<211> LENGTH: 10
<212> TYPE: PRT
<213> ORGANISM: Artificial
<220> FEATURE:
<223> OTHER INFORMATION: 10A

<400> SEQUENCE: 11

Gly Val Tyr Asp Gly Arg Glu His Thr Ala
1               5                   10

<210> SEQ ID NO 12
<211> LENGTH: 10
<212> TYPE: PRT
<213> ORGANISM: Artificial
<220> FEATURE:
<223> OTHER INFORMATION: 2.10A

<400> SEQUENCE: 12

Gly Ala Tyr Asp Gly Arg Glu His Thr Ala
1               5                   10

<210> SEQ ID NO 13
<211> LENGTH: 10
<212> TYPE: PRT
<213> ORGANISM: Artificial
<220> FEATURE:
<223> OTHER INFORMATION: 3M

<400> SEQUENCE: 13

Gly Val Met Asp Gly Arg Glu His Thr Val
1               5                   10

<210> SEQ ID NO 14
<211> LENGTH: 10
<212> TYPE: PRT
<213> ORGANISM: Artificial
<220> FEATURE:
<223> OTHER INFORMATION: 3F

<400> SEQUENCE: 14

Gly Val Phe Asp Gly Arg Glu His Thr Val
1               5                   10
```

```
<210> SEQ ID NO 15
<211> LENGTH: 10
<212> TYPE: PRT
<213> ORGANISM: Artificial
<220> FEATURE:
<223> OTHER INFORMATION: 5F

<400> SEQUENCE: 15

Gly Val Tyr Asp Phe Arg Glu His Thr Val
1               5                   10

<210> SEQ ID NO 16
<211> LENGTH: 10
<212> TYPE: PRT
<213> ORGANISM: Artificial
<220> FEATURE:
<223> OTHER INFORMATION: 5W

<400> SEQUENCE: 16

Gly Val Tyr Asp Trp Arg Glu His Thr Val
1               5                   10

<210> SEQ ID NO 17
<211> LENGTH: 10
<212> TYPE: PRT
<213> ORGANISM: Homo sapiens

<400> SEQUENCE: 17

Glu Val Tyr Asp Gly Arg Glu His Ser Ala
1               5                   10

<210> SEQ ID NO 18
<211> LENGTH: 10
<212> TYPE: PRT
<213> ORGANISM: Homo sapiens

<400> SEQUENCE: 18

Gly Leu Tyr Asp Gly Arg Glu His Ser Val
1               5                   10

<210> SEQ ID NO 19
<211> LENGTH: 10
<212> TYPE: PRT
<213> ORGANISM: Homo sapiens

<400> SEQUENCE: 19

Gly Val Tyr Val Gly Lys Glu His Met Phe
1               5                   10

<210> SEQ ID NO 20
<211> LENGTH: 10
<212> TYPE: PRT
<213> ORGANISM: Homo sapiens

<400> SEQUENCE: 20

Gly Leu Tyr Asp Gly Arg Glu His Leu Ile
1               5                   10

<210> SEQ ID NO 21
<211> LENGTH: 10
<212> TYPE: PRT
<213> ORGANISM: Homo sapiens

<400> SEQUENCE: 21

Gly Val Tyr Ala Gly Arg Glu His Phe Leu
1               5                   10
```

```
<210> SEQ ID NO 22
<211> LENGTH: 10
<212> TYPE: PRT
<213> ORGANISM: Homo sapiens

<400> SEQUENCE: 22

Gly Val Tyr Asp Gly Glu Glu His Ser Val
1               5                   10

<210> SEQ ID NO 23
<211> LENGTH: 10
<212> TYPE: PRT
<213> ORGANISM: Homo sapiens

<400> SEQUENCE: 23

Gly Leu Tyr Asp Gly Ile Glu His Phe Met
1               5                   10

<210> SEQ ID NO 24
<211> LENGTH: 10
<212> TYPE: PRT
<213> ORGANISM: Homo sapiens

<400> SEQUENCE: 24

Gly Val Tyr Ala Gly Arg Glu His Phe Val
1               5                   10

<210> SEQ ID NO 25
<211> LENGTH: 10
<212> TYPE: PRT
<213> ORGANISM: Homo sapiens

<400> SEQUENCE: 25

His Val Tyr Asn Gly Arg Thr His Gln Trp
1               5                   10

<210> SEQ ID NO 26
<211> LENGTH: 10
<212> TYPE: PRT
<213> ORGANISM: Homo sapiens

<400> SEQUENCE: 26

Arg Val Tyr Asp Gly Arg Glu Ile Leu Thr
1               5                   10

<210> SEQ ID NO 27
<211> LENGTH: 10
<212> TYPE: PRT
<213> ORGANISM: Homo sapiens

<400> SEQUENCE: 27

Gly Val Tyr Ser Gly Arg Ala His Pro Lys
1               5                   10

<210> SEQ ID NO 28
<211> LENGTH: 52
<212> TYPE: PRT
<213> ORGANISM: Artificial
<220> FEATURE:
<223> OTHER INFORMATION: MAGE-A4 Long Peptide
```

<400> SEQUENCE: 28

Asn Tyr Lys Arg Cys Phe Pro Val Ile Phe Gly Lys Ala Ser Glu Gly
1               5                   10                  15

Val Tyr Asp Gly Arg Glu His Thr Val Tyr Gly Pro Arg Lys Ala
            20                  25                  30

Glu Thr Ser Tyr Val Lys Val Leu Glu His Val Val Arg Val Asn Ala
        35                  40                  45

Arg Val Arg Ile
        50

<210> SEQ ID NO 29
<211> LENGTH: 9
<212> TYPE: PRT
<213> ORGANISM: Homo sapiens

<400> SEQUENCE: 29

Asn Tyr Lys Arg Cys Phe Pro Val Ile
1               5

<210> SEQ ID NO 30
<211> LENGTH: 21
<212> TYPE: PRT
<213> ORGANISM: Homo sapiens

<400> SEQUENCE: 30

Ala Glu Thr Ser Tyr Val Lys Val Leu Glu His Val Val Arg Val Asn
1               5                   10                  15

Ala Arg Val Arg Ile
            20

<210> SEQ ID NO 31
<211> LENGTH: 726
<212> TYPE: DNA
<213> ORGANISM: Artificial
<220> FEATURE:
<223> OTHER INFORMATION: MAGE #17

<400> SEQUENCE: 31
caggtccagc tggtacagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggaca atccaccgag cacagcctac     240
atggagctga gcagcctgag atctgaggac acggccgtgt attactgtgc gagatccccc     300
cggcgggcat atcatgatgc ttttgatatc tggggccaag ggacaatggt caccgtctct     360
tcaggtggag gcggttcagg cggaggtggc agcggcggtg gcgggagttc ctatgagctg     420
actcagccac cctcgatgtc agtgccccca ggaaagacgg ccagcattac ctgtggcgga     480
gaccatattg gaagtaaaag tgttcactgg taccagcaga agccaggcca ggcccctgta     540
ctggtcgtct atgatgatag cgaccggccc tcagggatcc ctgagcgatt ctctggctcc     600
aactctggga acacagccac tctgaccatc agcgggaccc aggctatgga tgaggctgac     660
tattactgtc tggcgtggga cagcagcact gcgatcttcg gcggagggac caagctgacc     720
gtcctc                                                                726

<210> SEQ ID NO 32
<211> LENGTH: 242
<212> TYPE: PRT
<213> ORGANISM: Artificial
<220> FEATURE:
<223> OTHER INFORMATION: MAGE #17

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Arg Arg Ala Tyr His Asp Ala Phe Asp Ile Trp Gly
            100                 105                 110

Gln Gly Thr Met Val Thr Val Ser Gly Gly Gly Ser Gly Gly
        115                 120                 125

Gly Gly Ser Gly Gly Gly Ser Ser Tyr Glu Leu Thr Gln Pro Pro
    130                 135                 140

Ser Met Ser Val Ala Pro Gly Lys Thr Ala Ser Ile Thr Cys Gly Gly
145                 150                 155                 160

Asp His Ile Gly Ser Lys Ser Val His Trp Tyr Gln Gln Lys Pro Gly
                165                 170                 175

Gln Ala Pro Val Leu Val Val Tyr Asp Asp Ser Asp Arg Pro Ser Gly
            180                 185                 190

Ile Pro Glu Arg Phe Ser Gly Ser Asn Ser Gly Asn Thr Ala Thr Leu
        195                 200                 205

Thr Ile Ser Gly Thr Gln Ala Met Asp Glu Ala Asp Tyr Tyr Cys Leu
    210                 215                 220

Ala Trp Asp Ser Ser Thr Ala Ile Phe Gly Gly Thr Lys Leu Thr
225                 230                 235                 240

Val Leu

<210> SEQ ID NO 33
<211> LENGTH: 363
<212> TYPE: DNA
<213> ORGANISM: Artificial
<220> FEATURE:
<223> OTHER INFORMATION: VH of MAGE #17

<400> SEQUENCE: 33
caggtccagc tggtacagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcggaca atccacgag cacagcctac     240 atggagctga gcagcctgag atctgaggac acggccgtgt attactgtgc gagatccccc     300
cggcgggcat atcatgatgc ttttgatatc tggggccaag gacaatggt caccgtctct     360 tca                                                                  363

<210> SEQ ID NO 34
<211> LENGTH: 51
<212> TYPE: DNA
<213> ORGANISM: Artificial
<220> FEATURE:
<223> OTHER INFORMATION: sc of MAGE#17

<400> SEQUENCE: 34
ggtggaggcg gttcaggcgg aggtggcagc ggcggtggcg ggagttccta t    51

<210> SEQ ID NO 35
<211> LENGTH: 312
<212> TYPE: DNA
<213> ORGANISM: Artificial
<220> FEATURE:
<223> OTHER INFORMATION: VL of MAGE#17

<400> SEQUENCE: 35
gagctgactc agccaccctc gatgtcagtg gccccaggaa agacggccag cattacctgt    60
ggcggagacc atattggaag taaaagtgtt cactggtacc agcagaagcc aggccaggcc   120
cctgtactgg tcgtctatga tgatagcgac cggccctcag ggatccctga gcgattctct   180
ggctccaact ctgggaacac agccactctg accatcagcg ggacccaggc tatggatgag   240
gctgactatt actgtctggc gtgggacagc agcactgcga tcttcggcgg agggaccaag   300
ctgaccgtcc tc                                                      312

<210> SEQ ID NO 36
<211> LENGTH: 121
<212> TYPE: PRT
<213> ORGANISM: Artificial
<220> FEATURE:
<223> OTHER INFORMATION: VH of MAGE#17

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Arg Arg Ala Tyr His Asp Ala Phe Asp Ile Trp Gly
            100                 105                 110

Gln Gly Thr Met Val Thr Val Ser Ser
        115                 120

<210> SEQ ID NO 37
<211> LENGTH: 17
<212> TYPE: PRT
<213> ORGANISM: Artificial
<220> FEATURE:
<223> OTHER INFORMATION: sc of MAGE#17

```
<400> SEQUENCE: 37

Gly Gly Gly Gly Ser Gly Gly Gly Ser Gly Gly Gly Gly Ser Ser
1               5                   10                  15

Tyr

<210> SEQ ID NO 38
<211> LENGTH: 104
<212> TYPE: PRT
<213> ORGANISM: Artificial
<220> FEATURE:
<223> OTHER INFORMATION: VL of MAGE#17

<400> SEQUENCE: 38

Glu Leu Thr Gln Pro Pro Ser Met Ser Val Ala Pro Gly Lys Thr Ala
1               5                   10                  15

Ser Ile Thr Cys Gly Gly Asp His Ile Gly Ser Lys Ser Val His Trp
                20                  25                  30

Tyr Gln Gln Lys Pro Gly Gln Ala Pro Val Leu Val Val Tyr Asp Asp
            35                  40                  45

Ser Asp Arg Pro Ser Gly Ile Pro Glu Arg Phe Ser Gly Ser Asn Ser
        50                  55                  60

Gly Asn Thr Ala Thr Leu Thr Ile Ser Gly Thr Gln Ala Met Asp Glu
65                  70                  75                  80

Ala Asp Tyr Tyr Cys Leu Ala Trp Asp Ser Ser Thr Ala Ile Phe Gly
                85                  90                  95

Gly Gly Thr Lys Leu Thr Val Leu
                100
```

ANTIGEN-BINDING PROTEIN THAT RECOGNIZES MAGE-A4-DERIVED PEPTIDE

CROSS-REFERENCE

This application is the US national stage of International Patent Application No. PCT/JP2018/021561 filed on Jun. 5, 2018, which claims priority to Japanese Patent Application No. 2017-111157 filed on Jun. 5, 2017.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
| --- | --- | --- |
| MIE009_SEQ_LIST1.txt | Mar. 3, 2020 | 13 |

TECHNICAL FIELD

The invention relates to the antigen-binding protein recognizing MAGE-A4-derived peptide and the like.

BACKGROUND ART

Currently, malignant tumors account for more than 30% of deaths, and are the leading cause of death in developed countries. Some cancers can be cured by advanced medical care, but others are difficult to treat. It is an urgent task to develop new treatments for cancer. For treating cancer, surgery, chemotherapy, and radiation therapy are three major therapies. Combination of the three therapies are used for treating cancer.

Recently, a fourth cancer therapy called immunotherapy has been progressed, the non-invasiveness and high effectiveness of the immunotherapy are focused. Immunotherapy is roughly classified in three types, i.e., vaccination, antibody therapy, and cell-transfusion-therapy. In cell-transfusion-therapy, two types therapies are known. One is the T-cell receptor gene transferred lymphocyte transfusion therapy, wherein T cell receptor (TCR) gene which reacts specifically cancer is induced to patient's lymphocytes in vitro and infused to the patient. The other is the specific T-cell transfusion therapy, wherein a chimeric antigen receptor (CAR) which contains scFv as antigen recognition site and CD3ζ as intracellular signal transduction molecule is transfused to patient's lymphocytes, and the lymphocytes are infused to the patient. In these treatments, since a large amount of lymphocytes comprising specificity to a cancer antigen are made by gene transduction in a short time, specific T cell therapies can be applied to various kinds of cancer patients.

The TCR gene infusion therapy, wherein the peptide MHC complex (pMHC) is recognized by T cells and cancer cells are killed, is safe and effective, and has been developed in the world. However, there is a problem that the killer T cell clones are extremely difficult to isolate.

On the other hand, there are three advantages to CAR infusion therapy. (1) Various patients can receive the therapy, since T cells transfected with CAR comprising single chain antibody (scFv) and T-cell receptor (TCR) and signaling domain of costimulatory molecules can recognize cancer antigen MHC-independently and attack cancer cells, different from the original T cells, (2) CD4-positive T cells as well as CD8-positive T cells and non-T cells may be affected to function, (3) higher affinity is hold compared to TCR, for the reactivity of an antibody inherits. Indeed, CAR therapy using anti-CD19 antibody has been reported with high clinical efficacy for patients with leukemia and lymphoma (Non-patent document 1: documents are summarized at the end). CD19 molecule is also expressed in B cells, the disappearance of B cells can be covered by supplement of immunoglobulin. In general, it is ideal to use antigens expressed only in cancer cells. However, there is a problem that such cell surface antigens have not been observed at present.

On the other hand, cancer specific antigens in intracellular molecules are reported, including cancer testis antigen and neoantigen. However, the CAR infusion therapy with cancer-specific intracellular antigens, has not been known.

In view of such circumstances, the inventors isolated antibodies that recognize the complex of MHC and intracellular antigens-derived-peptides, and constructed the CAR immunotherapy using the antibody. Only a few antibodies that specifically recognize the peptide/MHC complex have been reported (Non-patent document 2). If an antibody that specifically recognizes the peptide/MHC complex, and CAR-T cells which specifically kill cancer cells can be produced, it would become an innovative therapy. The CAR which recognizes the peptide/MHC complex can be used for infusion of CAR T cells, and when the peptide which is recognized specifically by the CAR-T cells is infused simultaneously, the proliferation of CAR-T cells can be expected by antigen presentation.

SUMMARY OF THE INVENTION

It is one non-limiting object of the present teachings to provide an antigen binding protein that specifically recognizes the MAGE-A4-derived peptide/HLA-A2 complex.

MAGE-A4 molecule was used as the antigen to be presented to MHC. MAGE-A4 is expressed in solid cancers including malignant melanoma (Non-patent document 3), and is CTA (cancer testis antigen) like NY-ESO-1. These molecules are expressed only in testis and placenta, not observed in other normal tissues. After MAGA-A4 is expressed in cells, it undergoes degradation in the proteasome. After degradation, MAGE-A4 peptides containing 10 amino acids are produced, are associated with HLA-A* 0201, beta-2 microglobulin in the endoplasmic reticulum, and are presented on the cell surface as a cancer-specific antigen. As the peptide presented on HLA-A* 0201, p 230-239 (GVYDGREHTV: SEQ ID NO:1) was selected (Non-patent document 4).

Methods to produce a CAR-T cell exhibiting a specific response to the target cancer by transfecting a CAR that specifically recognizes the A2-MAGE-A4 into human lymphocytes, and to apply the cell infusion therapy to human cells were established. (1) Antibodies that recognize the MAGE-A4-derived peptide and HLA-A2 complex with high affinity were isolated, (2) the specificity of the antibodies were examined, (3) antibodies with high specificity were screened, (4) CAR-T cells were prepared using the antibody, they were activated specifically by the target cancer cell, and cytotoxicity was caused, were confirmed. In a cancer therapy model using human tumor transplanted mice infused with CAR-T cells in vivo, it was observed that CAR-T cells specifically proliferated in the mouse body, and infiltrated into the tumor.

In one aspect of the present teachings, an antigen binding protein comprises the following polypeptide (A) or (B), and recognizes the HLA-A2-MAGE-A4 complex; (A) the polypeptide comprising the amino acid sequence of VH (heavy chain variable region) of SEQ ID NO; 36 and the amino acid sequence of VL (light chain variable region) of SEQ ID NO; 38; (B) polypeptides comprising an amino acid sequence having at least 90% homology with the VH (heavy chain variable region) of SEQ ID NO; 36 and an amino acid sequence having at least 90% homology with the VL (light chain variable region) of SEQ ID NO; 38. At this time, it is preferred that the antigen binding protein comprises the following polypeptide (C) or (D) between VH and VL: (C) the polypeptide comprising the amino acid sequence of a sc (single chain) of SEQ ID NO; 37; (D) a polypeptide comprising an amino acid sequence having at least 90% of the sc (single chain) of SEQ ID NO; 37. Further, it is preferred that the antigen binding protein comprises the polypeptide comprising the amino acid sequence of SEQ ID NO; 32, or a polypeptide having at least 90% homology with SEQ ID NO; 32. It is preferred that the antigen binding protein is a Fab, Fab', F(ab')$_2$, Fv or single chain Fv (scFv). In the specification, the antigen binding protein encompasses an antibody itself or an antibody derivative.

In the present teachings, homology means the relationship between two (or three or more) amino acid sequences or nucleotide sequences determined by comparing them. Homology means the degree of correlation determined by an alignment of amino acid sequences or nucleotide sequences, or between a series of partial sequences. Specifically, it is determined by the identity and retention of sequence (substitution to maintain the physicochemical properties of a particular amino acid or sequence in the sequence). The method to determine the homology is preferably one that contrasts the longest alignment between the sequences. To determine the homology, programs available on the Internet, for example, BLAST (Basic Local Alignment Search Tool) <https://blast.ncbi.nlm.nih.gov/Blast.cgi> are used. A polypeptide having at least 90% homology (preferably at least 95%, more preferably at least 98%) with SEQ ID NO: 32, 36, 37, 38 and recognizing the HLA-A2-MAGE-A4 complex is preferable.

In another aspect of the present teachings, a nucleic acid encodes the above-described antigen binding protein.

In another aspect of the present teachings, a vector comprises the above-mentioned nucleic acid, wherein the nucleic acid includes DNA or RNA. Nucleic acid can be either single stranded or double stranded. Vectors include a plasmid vector, and a virus vector as the like.

In another aspect of the present teachings, a chimeric antigen receptor includes the antigen binding protein and an intracellular domain of a signal transduction protein. In this aspect, the signal transduction protein is preferably any one of CD3zeta (CD3) chain and costimulatory molecules CD (GITR). Further comprising any one of the intracellular domain of CD28 and GITR is preferable.

In another aspect of the present teachings, a nucleic acid encodes the chimeric antigen receptor. In another aspect of the present teachings, a vector includes the nucleic acid.

In another aspect of the present teachings, a cell expresses the chimeric antigen receptor. In another aspect of the present teachings, a pharmaceutical composition comprises the cell as an active ingredient.

According to one or more aspects of the present teachings, an antigen binding protein specifically recognizing the MAGE-A4-derived peptide/HLA-A2 complex, nucleic acids encoding the antigen binding protein, vectors containing the nucleic acids, chimeric antigen receptors binding the antigen binding protein, nucleic acids encoding the chimeric antigen receptor, vectors containing the nucleic acids, cells expressing the chimeric antigen receptor, and pharmaceutical compositions comprising the cells are provided. The antigen binding protein specifically recognizing the MAGE-A4-derived peptide/HLA-A2 complex can be used in cell therapy and in the field of gene therapy. In addition, the protein is extremely useful for the detection of tumor cells expressing MAGE-A4-derived peptide/HLA-A2 complex, for treatment, research, and testing of the tumor. Furthermore, CAR-T cells of the present teachings can be used for an effective cancer therapy, since their side effects are small.

BRIEF DESCRIPTION OF THE FIGURES

FIG. 4 shows a graph of the measurements of KD values of MAGE #17 in which FIG. 4(A) shows the graph of dynamic changes in detective sensitivity over time, and FIG. 4(B) shows a table with the results of calculating the KD values based on the data read from the graph.

FIG. 20(B) is a graph showing the results of the effects of CAR-T cells against the A2-positive-MAGE-A4-negative tumors (HCT116).

FIG. 22(A) shows tumor sizes, and FIG. 22(B) shows body weights. Left arrows in the graphs show the treatment day of body irradiation (TBI) (day 3); right arrows show the lymphocytes administration date (day 4).

DETAILED DESCRIPTION

Figure 1:
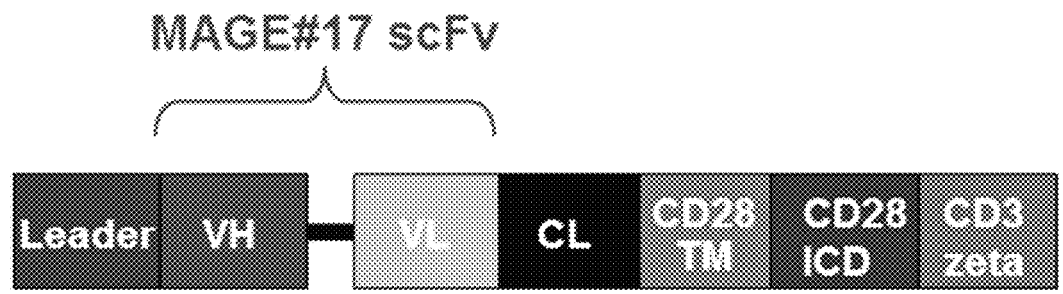
FIG. 1 shows the sequence image of MAGE #17 scFV.

Next, embodiments of the invention will be described with reference to the Figures and tables. The technical scope of the invention is not limited by these embodiments, and can be implemented in various forms without changing the gist of the invention.

In the specification, the terms "antibody" and "antigen-binding fragment" refer to antigen binding protein in the immune system. An antibody having an antigen-binding region is a glycoprotein comprising two heavy chains (H chains) and two light chains (L chains) linked each other by disulfide bonds. Each heavy chain includes a heavy chain variable region (VH) and a heavy chain constant region (CH). The heavy chain constant region is comprised of three domains, CH1, CH2 and CH3. Each light chain includes a light chain variable region (VL) and a light chain constant region (CL). VL is composed of CL domain. VII and VL regions can further be subdivided into complementarity determining regions (CDR) with hypervariability and framework regions (FR) with some extent conserved-sequence. In VII and VL, FR1, CDR1, FR2, CDR2, FR3, CDR3 and FR4, i.e. three CDRs and four FRs, are arranged from the amino terminus to the carboxyl terminus, respectively. For binding to antigen, CDR3 is known to be important. Both VII and VL comprise binding domains that interact with an antigen.

In the specification, the term "HLA" is Human Leukocyte Antigen (human leukocyte antigen), means the human major histocompatibility complex (MHC), and a complex of genes encoding cell surface molecules that are required for antigen presentation to immune cells. HLA can be classified into class I and class II. Class I HLA is composed of α-chain and β2-microglobulin. Class I HLA is expressed in almost all nucleated cells, and functions to CD8-positive T cells in antigen presentation. Class I HLA can be classified into HLA-A, HLA-B and HLA-C.

In the specification, the term "chimeric antigen receptor (CAR)" means a fusion protein containing an extracellular domain that binds to an antigen, a transmembrane domain different from the extracellular domain, and at least one intracellular domain. CAR can be called "chimeric receptor", "T-body", or "chimeric immune receptor (CIR)". "Extracellular domain that binds to an antigen" means any oligopeptide or polypeptide that binds to an antigen; "intracellular domain" means any oligopeptide or polypeptide that is known to function as a domain for a transmitting signal that activates or inhibits a biological process in a cell.

In the specification, "antigen binding protein" means a part of an antibody that binds to an antigen, or a fragment of an antibody that confers antibody specificity to the antigen.

Next, the embodiments of the present teachings will be specifically described.

(1) Antigen-Binding Fragments and Nucleic Acid Encoding them According to the Present Teachings The anti-MAGE-A4-derived peptide/HLA-A2 (HLA-A2-MAGE-A4) complex antibody is an antibody that specifically recognizes and binds to the complex of HLA-A2 and P230-239 (SEQ ID NO: 1), which is a peptide derived from HLA-A2-restricted MAGE-A4. Antibodies of the present teachings are highly specific, and do not bind to the complex of HLA-A2 and a peptide other than P230-239, or to the complex of P230-239 peptide and an HLA other than HLA-A2 (or exhibits very low binding activity). Thus, the antigen-binding fragment of the present teachings can specifically detect or target the HLA-A2-MAGE-A4 complex.

Antigen-binding fragments of the present teachings may contain (A) the polypeptide having the amino acid sequence of VII (heavy chain variable region) of SEQ ID NO: 36 and the amino acid sequence of VL (light chain variable region) of SEQ ID NO: 38, or (B) a polypeptide having an amino acid sequence for the VII (heavy chain variable region) with an amino acid sequence homology of 90% or more with respect to SEQ ID NO: 36, and an amino acid sequence for the VL (light chain variable region) with an amino acid sequence homology of 90% or more with respect to SEQ ID NO: 38. Antigen-binding fragment of the present teachings can contain (C) a polypeptide having the amino acid sequence of a sc (single chain) of SEQ ID NO: 37, or (D) a polypeptide having an amino acid sequence of sc (single chain) with an amino acid sequence homology of 90% or more with respect to SEQ ID NO: 37 between VII and VL.

Antigen-binding fragments of the present teachings include one or more fragments that specifically bind to an antigen. The fragment of an antibody comprising an antigen-binding region of the antibody specifically recognizes an antigen similar to the full-length antibody. As the antigen-binding fragments containing antibodies and fragments thereof, Fab, Fab', F(ab')$_2$, Fv and single chain Fv (scFv) are exemplified. Fab is a monovalent antibody fragment constituted from VL, VII, CL and CH1 domains. Fab' is a monovalent antibody fragment constituted from VL, VII, CL, CH1 domains, and a hinge region. F(ab')2 is a divalent antibody fragment comprising two Fab fragments linked by disulfide bonds of a hinge region. Fv is a monovalent antibody fragment constituted from VL and VII. VL and VII domains of Fv fragment are encoded by separate genes, scFv (which is a protein of one molecule) can be produced by gene recombination techniques by combining two genes with a linker. scFv contains a linker (single chain) between VII and VL. The sc connects VII and VL, and is a peptide commonly used in the present field to stabilize the antigen binding ability of scFv antibodies (e.g., Huston et al, Methods in Enzymology, 203: 46-88 (1991), Whitlow et al, Protein Eng., 6: 989 (1993)). Generally speaking, sc contains glycine and serine, and has a length of 15 to 18 amino acids.

One aspect of the present teachings comprises a combination of an antigen-binding fragment. For such molecules, Fab3, Diabody, Triabody, Tetrabody, Minibody, Bis-scFv, (scFv)2-Fc, intact-IgG are exemplified (Holliger et al., Nature Biotechnology, 23(9), p. 1126-36 (2005)).

One or several amino acids of antigen binding fragments may be modified, so long as it does not substantially affect its properties. For example, one or several amino acids in the constant region or FR region can be substituted, deleted, added or inserted. This modification can be easily performed by combining known methods that include site-directed mutagenesis (point mutation introduced and cassette mutagenesis, etc.), gene homologous recombination, primer extension, and PCR.

In one aspect of the present teachings, a nucleic acid encodes the antigen-binding fragment. Such an nucleic acid may comprise the nucleotide sequence shown in SEQ ID NO: 31 and 33 to 35 in the Sequence Listing. The nucleic acid can be modified to provide codons (optimal codon) suitable for host cells without changing the amino acid sequence encoded by the nucleic acid. The expression efficiency of a polypeptide in a host cell can be improved by modifying to provide optimum codons.

Such antigen-binding fragments can be prepared using known genetic engineering techniques or chemical synthesis methods. Such genetic engineering techniques include: preparing a cloning vector or an expression vector containing the appropriate nucleic acid, introducing the vector into a host cell, culturing host cells expressing the nucleic acid, and recovering the polypeptide by purification, whereby the polypeptide can be produced. In embodiments comprising a plurality of nucleic acids, a combination of a plurality of vectors each containing one pertinent nucleic acid molecule can be introduced into a host cell, or one vector comprising a plurality of nucleic acids can be introduced into a host cell. In preparing the polypeptide, if a peptide tag is linked to the polypeptide, the polypeptide can be recovered and purified using the peptide tag.

A vector according to the present teachings is operably linked to suitable control sequences to express the nucleic acids in a suitable host. Such control sequences contain a promoter to transcribe the nucleic acids, an operator sequence to control transcription, a sequence encoding a ribosome binding site, an enhancer, a polyadenylation sequence, and a sequence for controlling termination of transcription and translation and the like. Various known sequences (e.g., restriction enzyme cleavage site(s), marker gene(s) such as drug resistance genes (selection genes), signal sequence(s), leader sequence(s), and the like) can be used in the vector. Various sequences can be selected and used appropriately according to the type of expressed polypeptide, the host cell, the conditions of the medium and the like.

A vector that is incorporated into the host genome, or is not incorporated the host genome, and an episomal vector that exists in the cytoplasm to replicate autonomously and the like can be used in the invention. As a vector, a retrovirus vector (containing oncoretrovirus vectors, lentivirus vectors, pseudotyped vector), adenoviral vector, adeno-associated virus (AAV) vector, simian virus vector, vaccinia virus vector, Sendai virus vector, Epstein-Barr virus (EBV) vector, HSV vector and the like are exemplified. As a virus vector, viruses that lack replication ability in the infected cells can be preferably used. Further, non-virus vectors can also be used by combination with a liposome and a condensing agent such as cationic lipids. Furthermore, the nucleic acid can be introduced into cells by performing calcium phosphate transfection, DEAE-dextran, electroporation, particle bombardment or the like.

As the host cell, known host cells can be used. For example, prokaryotic cells such as $E.\ coli$, mammalian cells such as Chinese hamster ovary cells (CHO cells), human cells, and eukaryotic cells such as yeast and insect cells and the like are exemplified.

If the antigen-binding fragment is expressed in a host cell, it can be purified from host cell medium, extracts and/or lysate of host cells. Purification methods can be performed by combining appropriate known methods. For example, centrifugation, hydroxyapatite chromatography, gel electrophoresis, dialysis, fractionation on an ion-exchange column, ethanol precipitation, reversed phase HPLC, chromatography by silica, chromatography by heparin sepharose, anion or cation resin chromatography (polyaspartic acid column, etc.), chromatofocusing, SDS-PAGE, ammonium sulfate precipitation, and affinity chromatography can be used appropriately.

(2) Compositions According to the Present Teachings

In other aspects of the present teachings, a composition may comprise one or more of the antibodies or the antigen-binding fragments described above in section (1), and/or a composition may comprises a nucleic acid encoding the antibody or the antigen-binding fragment(s).

Such an antibody or antigen-binding fragment can be used as a probe for the MAGE-A4-derived peptide and HLA-A2 complex. MAGE-A4 is known to be expressed inside cancer cells and be presented by HLA; T cells attack the cancer cells based on antigen recognition. Therefore, antigen-binding fragments of the present teachings can be used as a probe for cancer cells, i.e. a detection or diagnostic composition.

For such detection methods, known detection methods, such as ELISA, fluorescent antibody assay, radioimmunoassay, radioimmunoprecipitation, dot blot assays, inhibition or competition assay, sandwich assay, and latex beads agglutination assays, can be exemplified.

Samples for diagnosis and detection contain biological samples (e.g. disease site tissues, cells, body fluid containing blood, serum, plasma, lymph, and urine). For these samples, after having been pre-purified, homogenized, centrifuged, or diluted in a suitable buffer, if necessary, contacted to a antigen-binding fragment according to the present teachings, an antigen-antibody complex is detected. In this case, the antigen-binding fragment can be labeled, or a labeled secondary antibody can used. For the label, an enzyme (such as horseradish peroxidase, alkaline phosphatase, etc.), radioactive isotopes (e.g. $^{32}P$, $^{35}S$, $^{3}H$, $^{125}I$, etc.), fluorescent substance (e.g. rhodamine, fluorescamine, dansyl chloride, and their derivatives etc.), and tag peptide and the like can be used.

Such antigen-binding fragments can be used to deliver a pharmaceutical composition to a target. The antibody or the antigen-binding fragment may be linked to a pharmaceutical that specifically recognizes the WT1 peptide and HLA-A24 complex. For a pharmaceutical composition for delivery to a target, cytokines (IL2, TNF, IFN-γ etc.), receptor proteins of them, cytotoxin (ricin, diphtheria, gelonin etc.), radioactive isotopes ($^{90}$Y, $^{131}$I, $^{225}$Ac, $^{213}$Bi, $^{223}$Ra and $^{227}$Th etc.), cells (T cells, NK cells, etc.) or low molecular weight compound (calicheamicin, doxorubicin etc.) are exemplified.

Effective amounts of the active ingredients of the pharmaceutical composition of the present teachings are determined appropriately based on the purpose, the tumor type, the medical conditions such as decease site and size of the patient's condition, and administration route and the like. When used as a pharmaceutical composition, various components that may be accepted pharmaceutically (e.g., carrier, excipient, buffer, stabilizer, etc.) can be added in addition to the active ingredient. The pharmaceutical composition may be provided in the form of a tablet, liquid, powder, gel, spray, a microcapsule, colloidal distribution system (liposomes, microemulsions, etc.), and macroemulsion as the like based on the conditions. As an administration route of the pharmaceutical composition, intravenous, intraperitoneal, intracerebral, intrathecal, intramuscular, intraocular, intraarterial, bile duct, and intralesional injection, infusion, sustained release systems formulation and the like are exemplified. The pharmaceutical composition can be administered by continuous infusion or injection.

Pharmaceutical compositions according to the present teachings can be used for treating hematopoietic tumors such as chronic myeloid leukemia, acute lymphocytic leukemia (ALL), and acute myeloid leukemia (AML), and solid cancers such as stomach cancer, colon cancer, lung cancer, breast cancer, germ cell cancer, live cancer, skin cancer, bladder cancer, prostate cancer, uterine cancer, cervical cancer, ovarian cancer, mesothelioma and the like, and for the diagnosis and detection of tumors and solid cancers. In particular, it is useful for the treatment, diagnosis and detection of MAGE-A4-positive or HLA-A2 positive hematopoietic tumor and solid cancer.

(3) Chimeric Antigen Receptor According to the Present Teachings

In a further aspect of the present teachings, a chimeric antigen receptor (CAR) may comprise one or more antigen-binding fragments described above in section (1) and an intracellular domain of a signaling protein. When a CAR that specifically recognizes the HLA-A2-MAGE-A4-derived-peptide complex binds to it, a signal can be transmitted to cells expressing CAR. CAR comprises an extracellular domain, a transmembrane domain and an intracellular domain. In the extracellular domain, an antigen binding fragment of the present teachings is contained. When the extracellular domain binds to the HLA-A2-MAGE-A4 complex specifically, a signal is transmitted into the cell via the intracellular domain of CAR, and stimulates the cell expressing CAR. Stimulated cells produce cytokines and the like, exhibit cytotoxicity to the target cells expressing the complex, or induce cytotoxicity of other immune cells.

As an intracellular domain of CAR, a domain that can transmit a signal into the cell, when the extracellular domain of the CAR molecule interacts (binds) to the MAGE-A4-derived peptide/HLA-A2 complex, can be used. As such signaling proteins, membrane proteins, signal receptors, and cytokine receptors are exemplified. For the intracellular domain of CAR, the intracellular domains containing a primary cytoplasmic signal transmitting sequence derived from CD3zeta (CD3ζ), FCRγ, FcRβ, CD3γ, CD3δ, CD3ε, CD5, CD22, CD79a, and CD66d are exemplified. Further, the intracellular domains containing a secondary cytoplasmic signal (costimulatory signal) transmitting sequence derived from CD2, CD4, CD5, CD8α, CD8β, CD28, CD137 (also known as "4-1BB"), CD134, ICOS, GITR and CD154 are exemplified. Furthermore, the intracellular domains containing a tertiary cytoplasmic signal transmitting sequence derived from IL-2 receptor and IL-21 receptor are exemplified.

As a transmembrane domain of CAR, alpha chain or beta chain of T-cell receptor, the transmembrane domain of CD3 zeta chain, CD28, CD3ε, CD45, CD4, CD5, CD8, CD9, CD16, CD22, CD33, CD37, CD64, CD80, CD86, CD134, CD137 (also known as "4-1BB"), ICOS, CD154, and GITR and the like can be used. Artificially designed sequence can be used.

Further aspects of the present teachings include a nucleic acid that encodes a CAR. Nucleic acid encoding a CAR can be connected with another nucleic acid to be expressed under the control of a suitable promoter. A promoter that is expressed constitutively, or expressed inducibly by drug (e.g., tetracycline or doxorubicin) can be used. For example, mammalian-derived promoter containing phosphoglycerate kinase (PGK) promoter, Xist promoter, beta-actin promoter, and RNA polymerase II promoter, virus-derived promoter containing SV40 early promoter, cytomegalovirus promoter, thymidine kinase promoter of herpes simplex virus, LTR promoter of various retrovirus and the like can be used. To achieve efficient transcription of the nucleic acid, another regulatory element which cooperates with a promoter or a transcription initiation site (e.g., an enhancer sequence or a terminator sequence) can be linked to the nucleic acid. Furthermore, a marker gene which can be used for confirmation of the expression of the nucleic acid (e.g., drug resistance gene, a gene encoding a reporter enzyme, or a gene encoding a fluorescent protein etc.) can be incorporated.

Nucleic acid encoding the CAR can be introduced into cells by a vector. Moreover, nucleic acid encoding the CAR may be used as an active ingredient of a pharmaceutical composition. A pharmaceutical composition comprising the nucleic acid encoding the CAR can be prepared and used in accordance with the description in section (2) above.

In another aspect of the present teachings, a cell that express the CAR is included. The cells can be prepared by a process of introducing an appropriate CAR into a cell. When a cell expressing the CAR binds to the HLA-A2-MAGE-A4 complex via the CAR, a signal is transmitted to the cell and activated. Activation of cells can be confirmed by the release of cytokines, increased proliferation rate, the change of cell surface molecules and the like, depending on the host cell type and the intracellular domain. For example, the release of cytotoxic cytokines (tumor necrosis factor, lymphotoxin etc.) from activated cells results in the destruction of tumor cells expressing the complex. Further, cytokine release and the change of cell surface molecules stimulates other immune cells, for example, B cells, dendritic cells, NK cells, macrophages and the like. Thus, CAR expressing cells are useful for adoptive immunotherapy, especially against MAGE-A4-positive, HLA-A2 positive tumors or cancer.

The process of introducing the nucleic acid encoding the CAR into cells is carried out in vitro (ex vivo) or in vivo. For cells introduced by nucleic acid, mammalian cells such as human-derived cells, and non-human mammal-derived cells containing monkey, mouse, rat, pig, cow, and dog, etc. can be used. For types of cells, for example, cells from body fluid such as blood (peripheral blood, umbilical cord blood, etc.), bone marrow, tissue or an organ, collected, isolated, purified, and induced can be used. PBMCs, immune cells (dendritic cells, B cells, hematopoietic stem cells, macrophages, monocytes or NK cells, blood cells (neutrophils, basophils, monocytes), hematopoietic stem cells, cord blood mononuclear cells, fibrosis blasts, preadipocytes, hepatocytes, blood cells, skin keratinocytes, mesenchymal stem cells, hematopoietic stem cells, adipose stem cells, pluripotent stem cells, various cancer cell lines or neural stem cells can be used. In the invention, particularly T cells, T cell precursors (hematopoietic stem cells, lymphoid progenitor cells, etc.), pluripotent stem cells or cell populations containing them are used preferably. T cells contain CD8-positive T cells, CD4-positive T cells, regulatory T cells, cytotoxic T cells, tumor infiltrating lymphocytes. The cell population containing T cells and progenitor cells of T cells include PBMCs. Cells used in the invention can be any of cells sampled from living body, those expanded by culture, and cell lines. When cells transfected a nucleic acid or differentiated cells from them can be expected to be transplanted into a living body, cells collected from the living body or the same kind of living body are preferably transplanted.

For cells expressing a CAR according to the present teachings, culture and/or stimulation with the appropriate culture medium and/or stimulatory molecules prior to administration to a subject can be performed. Examples of the stimulatory molecules include cytokines, appropriate proteins, and other components. As cytokines, for example, IL-2, IL-7, IL-12, IL-15, and IFN-γ and the like are exemplified, preferably IL-2 is exemplified. The concentration of IL-2 in the medium is not particularly limited; for example, the concentration is $0.01-1 \times 10^5$ U/mL, preferably $1-1 \times 10^4$ U/mL. Also, as suitable proteins, CD3 ligand, CD28 ligand, and anti-IL-4 antibody are exemplified. In addition, lymphocyte stimulator such as lectins can be added. In addition, serum or plasma can be added to the culture medium. The amount of the additives to the medium is not particularly limited; 0-20% by volume is exemplified, and the amount of serum or plasma can be changed accordance with the culture stage. The concentration of serum or plasma can be decreased stepwise. The origin of the serum or plasma can be the same as self (the same origin as cultured cells) or can be non-self (different from the origin of cultured cells), preferably those from self are used for the sake of safety.

The cell culture equipment to be used for cell culturing is not particularly limited; for example, a petri dish, a flask, a bag, a large culture bath, a bioreactor and the like can be used. As the bag, a cell-culture-$CO_2$ gas-permeable bag can be used. When a mass of cell populations is produced industrially, a large culture bath can be used. Further, the culture can be conducted in an open system or a closed system; a closed system is preferably used for safety of the resulting cell population.

In another aspect of the present teachings, a pharmaceutical composition may contain cells that express an CAR according to the present teachings as an active ingredient and may be administered parenterally. As parenteral administration, intravenous, intraarterial, intramuscular, intraperitoneal, and subcutaneous administration and the like are exemplified. To increase the anti-tumor effect, administration to meningioma or nearby tissue, for example, subcutaneous administration, can be used. The administration dose is suitably selected depending on the subject's condition, weight, age and the like. Usually, as the number of cells, $10^7$-$10^9$ cells per 60 kg body weight per administration, preferably about $5 \times 10^7$-$5 \times 10^8$ cell, are administered. The pharmaceutical composition can be administered one time or multiple times. The pharmaceutical composition can be in a form suitable for parenteral administration, for example an injection or infusion. The pharmaceutical composition can optionally comprise a pharmaceutically acceptable excipient. The pharmaceutical composition can comprise saline, phosphate buffered saline (PBS), medium or the like, in order to maintain cells stably. The medium is not particularly limited; RPMI, AIM-V, X-Vivo 10 and the like are generally exemplified.

<Test Method>
1. Antibody Screening with Human Antibody Phage Library
(1) Preparation of pMHC Beads 20 μg of A2-MAGE-A4 as pMHC and 200 mg of magnetic beads bound with Streptavidin were mixed and reacted at 4° C. in 0.05% Tween/PBS(−) solution. 3 μL of 2 mM biotin/PBS(−) was added and reacted for 1 hour. The solution was washed twice by 0.05% Tween/PBS(−), and suspended in 400 μL of 0.05% Tween/PBS(−). The suspension was used as the antigen beads.

(2) Human Antibody Library

VH and VL were amplified by PCR from tonsils, umbilical cord blood, peripheral blood, and bone marrow from dozens of healthy individuals. The PCR products were recombined to the phagemid vector pUC119, to make scFv with repertoire of $3.4 \times 10^{12}$. The scFv was displayed on cp3 of M13 phage. The product was used as a human antibody library.

(3) Screening Using Human Antibody Library, Isolation of Antibodies, Preparation of Cp3 Culture Supernatant The reaction mixture containing $3.4 \times 10^{12}$ cfu of human antibody library solution, 100 μg of Streptavidin (Pierce), 30 μg of A2-CMV tetramer, 30 μg of A2-Foxp69 tetramer, 30 μg of A2-IDOp41 tetramer, 30 μg of A2-IDOp195 tetramer, 20 μg of Gamma guard, 100 μL of 2% BSA solution, 65 μL of 10% TritonX100, 1000 μL of 1% TritonX100/PBS was prepared and mixed and rotated for 1 hour at room temperature and 100 μl of magnetic beads solution which was bound to A2-MAGE-A4 tetramer was added and mixed and rotated for 1 hour. Then, the magnetic beads were trapped with Magnet Trapper (Toyobo), while being washed 5 times with 1% TritonX100/PBS. The magnetic beads were added to cultured XL1-blue, infected 1 hour at 37° C., centrifuged, and suspended in 600 μL of 2×YTAG medium (200 μg/mL ampicillin, 1% glucose/2×YT). The suspension was plated on YTAG agar plate (200 μg/mL ampicillin, 2% glucose/ nutrient agar (Nissui)), and cultured for 15 hours at 37° C. Colonies were harvested with 30 mL of 2×YTAG medium, 200 μL of the harvested solution was added to 20 mL of 2×YTAG medium, and 30 μL of helper phage VCSM was added. The mixture was incubated for 30 minutes at 37° C. for infection, and incubated for 90 minutes at 37° C. 80 mL of 2×YTAG medium, 60 μL of 50 μg/mL kanamycin, and 50 μL of 1M IPTG were added to the cultured mixture, and incubated for 20 hours at 28° C. After the incubated mixture was centrifuged, the supernatant was mixed with 25 mL of PEG solution (20% PEG #600, 2.5M NaCl). The precipitate was collected by centrifugation, was suspended in 1 mL PBS, and sterilized with filter. The operation was repeated two times. Recovered E. coli were plated on YTAG agar medium. After being incubated at 30° C., colonies were picked up and cultured in LB medium at 30° C. overnight. DNA was extracted by Miniprep DNA Kit (QIAGEN) using a portion of the cultured LB medium, and sequenced. The, 50 μL of the culture was mixed with 1.5 mL of 2×YTAI (2×YT medium containing 0.5 mM of IPTG), and cultured at 30° C. overnight. The supernatant was separated by centrifugation. The supernatant was used as cp3 supernatant. ELISA was conducted by using the cp3 supernatant.

2. Enzyme-Linked Immunosorbent Assay (ELISA)

(1) MHC-Peptide Complex (Monomer)

The complex that HLA-A*0201 bound to MAGE-A4 p230, MAGE-A4 P286, MAGE-A3 P195, CMV, MelanA, GP3, HTLV-1, NY-ESO-1 p157, NY-ESO-1 p159, Foxp3 p69, Foxp3 p127, Foxp3 p390, IDO p41, IDO p41, IDO p195, and IDO p199 were used as MHC-peptide complex.

(2) Immobilization of pMHC 500 ng of neutraavidin (PIERCE Co.) in 50 µL of PBS was suspended in Maxisorp loose (Nunc), and was shaken at 4° C. overnight. After discarding the solution, 200 µL of 2% BSA/PBS was added and the solution was placed and blocked overnight. After discarding the solution, 300 ng of HLA-A2-MAGE-A4 monomer in 50 µL of PBS was added and shaken at 4° C. overnight. The solution was washed with PBS.

Immobilization of HLA-A2-CMV as a negative control was conducted in the same manner.

(3) Measurement of ELISA Reaction

100 µL of cp3 culture supernatant was poured into the immobilized antigen plate well, after shaking for 1 hour at room temperature, the plate well was washed with PBS, 100 µl of anti-cp3 rabbit antibody diluted 2000-fold with 0.05% Tween20/PBS was poured into the well, and the plate was shaken for 1 hour at room temperature. After the well was washed with PBS, 100 µl of HRP-labeled anti-rabbit IgG (MBL Co., Ltd.) at 4000-fold diluted in 0.05% Tween20/PBS was poured into the well, and the plate was shaken for 1 hour at room temperature. After the well was washed with PBS, OPD (WAKO Co., Ltd.) suspended in 0.01% 11202, 0.1M $Na_2PO_4$, 0.1M citric acid (p115.1) was poured and reacted, after confirming color development, 2N $H_2SO_4$ was added to stop the reaction. The absorbance was measured at 490 nm wavelength at SpectraMaxM2 (molecular devices).

3. Purification of Antibody (1) Transfection to the Vector for Purification

Antibody gene was transferred to His/FLAG expression vector for changing to the form of scFv-FLAG/His. FLAG tag was used for detection by FACS, His-tag was used for purification by column, respectively.

(2) Transformation

After the isolated antibody cloned DNA was reacted by SalI (Takara Bio Inc.), the DNA fragment was reacted with the vector by T4 DNA ligase. Competent cells DH5a (TOYOBO Co. Ltd.) was transformed by the DNA, and was plated on LBGA plate. After incubated at 30° C. overnight, colonies were cultured in 2×YTAG, and part of the culture solution was cultured in 2×YTAI, supernatant was prepared by centrifugation.

(3) Confirmation of scFv-FLAG/His Expression

After 100 µl of culture supernatant was poured in a well of antigen plate, shaking for 1 hour at room temperature and the well was washed with PBS. For confirmation of expression of His-tag, HRP-labeled anti-His (MBL Co., Ltd.) at 4000-fold diluted in 0.05% Tween20/PBS was poured and shaken for 1 hour at room temperature. For confirmation of expression of FLAG-tag, anti-FLAG(DDDK) antibody, and HRP-labeled antibody were reacted in the order.

After the antigen plate was washed with PBS, OPD (WAKO Co., Ltd.) suspended in 0.01% $H_2O_2$, 0.1M $Na_2PO_4$, 0.1M citric acid (pH5.1) was poured and reacted, after confirming color development, 2N $H_2SO_4$ was added to stop the reaction. The absorbance was measured at 490 nm wavelength at SpectraMaxM2 (molecular devices).

(4) Crude Purification of Antibody 2 mL of pre-cultured bacterial solution was put into 100 mL of 2×YTAI, and cultured at 30° C. overnight. The solution was centrifuged (8000 rpm, 10 min, 4° C.)., the supernatant was collected, 100 mL of saturated sulfuric acid were added to the supernatant, and stirred. The solution was centrifuged (8000 rpm, 20 min, 4° C.), and the precipitate was suspended in 10.5 mL of PBS complete. After the PBS complete was centrifuged (12000 rpm, 1 h, 4° C.)., 1 mL of Ni Sepharose excel (GE Healthcare) equilibrated with PBS was added to the supernatant, and incubated at 4° C. overnight. A column was filled with the sample, washed with 0.5M NaCl PBS containing 0.5M NaCl PBS and 20 mM imidazole, and eluted with 0.5M NaCl PBS containing 250 mM imidazole. The eluent was dialyzed against PBS, after the dialysis, was concentrated with Amicon Ultra 10K (Millipore). SDS-PAGE was conducted with a part of the sample, to confirm the band by CBB staining, to determine the protein concentration of the crude purified antibody.

(5) Purification of His-Tag Protein Using AKTA Prime Plus

The crude antibody was further purified using HisTRAP column by AKTA Prime plus (GE Healthcare). The procedure was carried out according to the attached His-tag purification protocol. The recovered peak fractions were detected by SDS-PAGE.

4. Measurement of the Dissociation Constant (KD Value)

KD values of purified antibodies were measured by BiacoreX100 (GE Healthcare). Immobilization of ligands was conducted with Biotion capture kit (GE Healthcare).

(1) Immobilization of Ligand

HLA-A2-MAGE-A4 p230 was immobilized to the sensor chip CAP. The concentration was adjusted to 200 nM with HBS buffer, and the ligand was immobilized as suitable RU (resonance unit).

(2) Preparation of the Analyte Solution

Purified antibody was adjusted to 12.5 nM, 25 nM, 50 nM, 100 nM and 200 nM with HBS EP+buffer.

(3) Measurement of KD Values

The binding reaction was measured for 180 seconds while analyte solution was flowing through the flow cell of sensor chip. After the measurement, analyte solution was switched to HBS buffer, and the dissociation reaction was measured for 300 seconds. The measurement was carried out using a single cycle method of the program to flow continuously analyte from low concentration to high concentration.

After the reactions has ended with all concentrations, the binding constant were calculated using the curve fitting program.

5. Flow Cytometry Analysis (FACS)

(1) Equipment

FACS Calibur/FACS Cant/FACS Cantll (BD) were used to measure flow cytometer.

(2) Fluorescence-Labeled Antibody

Fluorescent-labeled antibodies were used as described in Table 1.

TABLE 1

| Fluorescent label | Antigen | Clone ID. | Company |
| --- | --- | --- | --- |
| FITC | CD8 | HIT8a | BD bioscience |
| APC | CD4 | RPA-T4 | Biolegend |
| APC | CD8 | RPA-T8 | Biolegend |
| APC | 107a | H4A3 | Biolegend |
| APC-Cy7 | CD4 | RPA-T4 | Biolegend |
| APC-Cy7 | CD8 | RPA-T8 | Biolegend |
| perCP-Cy5.5 | CD8 | RPA-T8 | Biolegend |
| PE-Cy7 | TNF-α | MAb11 | eBioscience |
| V450 | IFN-γ | 4S.B3 | eBioscience |

(3) Tetramer PE

Tetramer PE means the streptavidin-PE to which four biotinylated monomers are attached. The tetramer PE was used for detection of antigen-specific T cells. Tetramers used in the specification were A2-MAGE-A4 p230 tetramer and A2-NY-ESO-1 p157 tetramer.

6. HLA Stability Assay and scFv Binding Assay (1) T2 Cell (HLA-A*02+Human BT Hybrid Lymphoblastoid Cell Line)

T2 cell is a kind of cell line that lacks Transporter Associated with Antigen Processing (TAP), has a specificity which the intracellular protein is not presented to HLA.

(2) Peptide Pulse to T2 Cells

Peptide was added to a final concentration of 10 μM to T2 cells in human RPMI1640, placed for 15 minutes at room temperature, 20% FCS human RPMI1640 was added to a final concentration of 10% FCS. The cells were incubated in $CO_2$ incubator for 45 min. at 37° C. After two washes, the cells were used to assay.

(3) HLA Stability Assay

Anti-HLA-A2 Alexa Fluor 488 was reacted with peptide-pulsed T2 cells for 1 hour, the amount of HLA stabilized on the T cell surface was determined by detecting with FACS.

(4) scFv Binding Assay

Peptide-pulsed T2 cells were reacted with acquired antibodies for 1 hour, with anti-FLAG antibody for 1 hour, with anti-mouse FITC antibody for 1 hour, and they were detected with FACS.

(5) One Amino Acid Substituted Peptides and Risk Peptide

As shown in Table 2, one amino acid substituted peptides wherein one of 10 amino acids of MAGE-A4p230-239 was substituted with alanine (A), methionine (M), phenylalanine (F) and tryptophan (VV) were synthesized and examined IC50 of each peptide. Each peptide was adjusted to a final concentration of 10 mM in DMSO.

MHC IC50 is the theoretical value calculated by the IEDB (http://tools.immuneepitope.org/processing/), and when the value is lower, it is indicated that the bond between HLA-A*0201 and the peptide is stronger.

Table 2 shows the amino acid sequence of one amino acid substituted peptides and IC50.

TABLE 2

| I.D. | Amino acid sequence | MHC IC50 (nM) |
| --- | --- | --- |
| MAGE-A4p230-239 (SEQ ID NO: 1) | GVYDGREHTV | 225.4 |
| 1A (SEQ ID NO: 2) | AVYDGREHTV | 118.1 |
| 2A (SEQ ID NO: 3) | GAYDGREHTV | 2482.2 |
| 3A (SEQ ID NO: 4) | GVADGREHTV | 1139.1 |
| 4A (SEQ ID NO: 5) | GVYAGREHTV | 437.6 |
| 5A (SEQ ID NO: 6) | GVYDAREHTV | 330.9 |
| 6A (SEQ ID NO: 7) | GVYDGAEHTV | 75.0 |
| 7A (SEQ ID NO: 8) | GVYDGRAHTV | 108.9 |

TABLE 2-continued

| I.D. | Amino acid sequence | MHC IC50 (nM) |
| --- | --- | --- |
| 8A (SEQ ID NO: 9) | GVYDGREATV | 289.1 |
| 9A (SEQ ID NO: 10) | GVYDGREHAV | 197.0 |
| 10A (SEQ ID NO: 11) | GVYDGREHTA | 2323.2 |
| 2.10A (SEQ ID NO: 12) | GAYDGREHTA | 10668.2 |
| 3M (SEQ ID NO: 13) | GVMDGREHTV | 148.6 |
| 3F (SEQ ID NO: 14) | GVFDGREHTV | 169.8 |
| 5F (SEQ ID NO: 15) | GVYDFREHTV | 119.8 |
| 5W (SEQ ID NO: 16) | GVYDWREHTV | 119.8 |
| A2-CMV | | 21.29 |

Table 3 shows the amino acid sequence of risk peptides and IC50 values which were extracted from MAGE family peptide and amino acid recognizing MAGE #17 antibody by BLAST search.

TABLE 3

| Risk Peptide | Amino acid sequence | MHC IC50 (nM) |
| --- | --- | --- |
| MAGE-A4 (SEQ ID NO: 1) | GVYDGREHTV | 225.4 |
| MAGE-A1 (SEQ ID NO: 17) | EVYDGREHSA | 13523.5 |
| MAGE-A8 (SEQ ID NO: 18) | GLYDGREHSV | 9.7 |
| MAGE-A9 (SEQ ID NO: 19) | GVYVGKEHMF | 35519.6 |
| MAGE-A10 (SEQ ID NO: 20) | GLYDGREHLI | 35.4 |
| MAGE-A11 (SEQ ID NO: 21) | GVYAGREHFL | 736.5 |
| MAGE-B2 (SEQ ID NO: 22) | GVYDGEEHSV | 110.5 |
| MAGE-B10 (SEQ ID NO: 23) | GLYDGIEHFM | 10.2 |
| MAGE-C2 (SEQ ID NO: 24) | GVYAGREHFV | 156.2 |
| ADAMTS (SEQ ID NO: 25) | HVYNGRTHQW | 36230.3 |
| RBBP5 (SEQ ID NO: 26) | RVYDGREILT | 5880.0 |
| Calcyphosin (SEQ ID NO: 27) | GVYSGRAHPK | 35865.8 |

7. Construction of CAR Construct and Vector
(1) MAGE #17 28z CAR

FIG. 1 shows the sequence image of the construction of CAR. The construct contains Leader, VH, VL, CL, CD28TM, CD28ICD (intracellular domain of CD28) and CD3zeta (CD3) chains from the 5' end. VII and VL is MAGE #17 scFv in these chains.

(2) Construction of CAR

Figure 2:
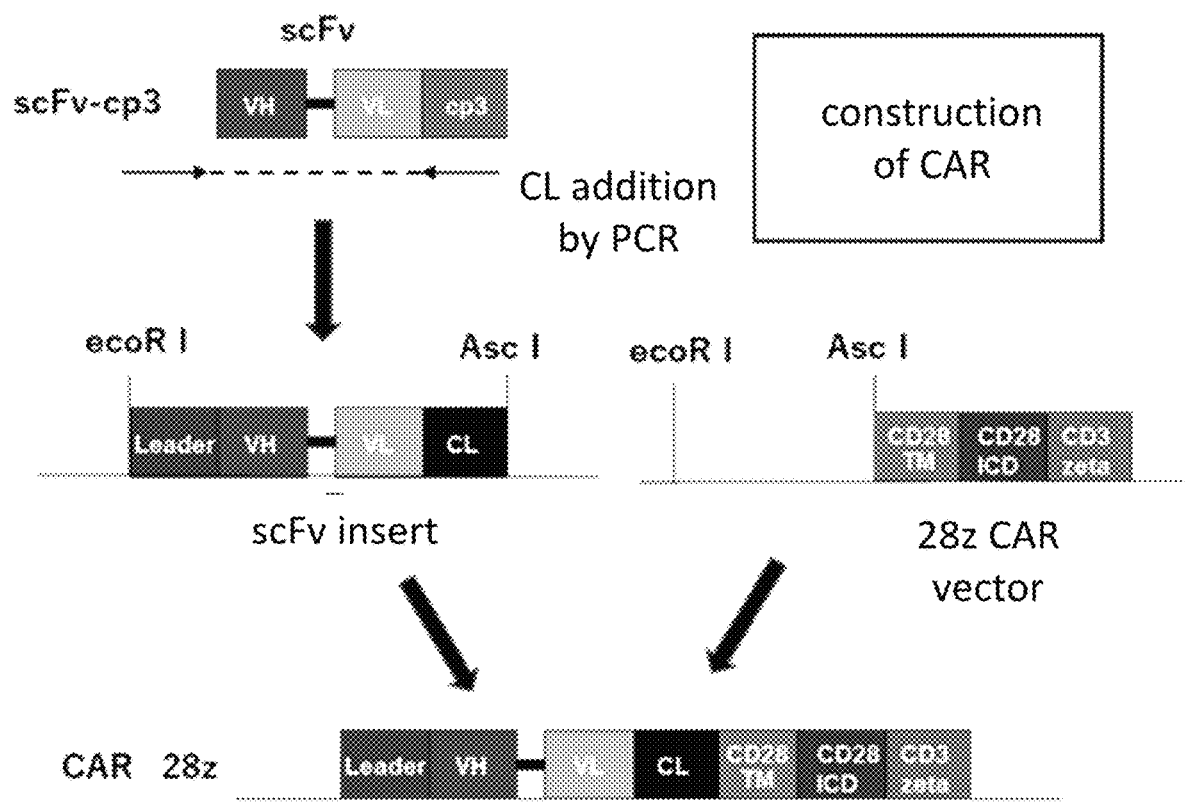
FIG. 2 shows the gene sequence image for explaining the construction method of CAR.

FIG. 2 shows the construction steps of CAR schematically. To explain each step is as follows.

First, the PCR reaction was conducted using scFv-cp3 as a template, wherein Leader with EcoRI recognition site in 5' end of the VH-VL and CL with AscI recognition site in 3' end were added, respectively. Next, the fragment of PCR product treated with EcoRI and AscI, and the fragment of 28z CAR vector treated with EcoRI and AscI were reacted by ligase to obtain CAR 28z.

8. Preparation of Human Lymphocytes

Human lymphocytes were prepared from healthy donor blood using Ficoll-PaqueTM PLUS (17-1440-03, GE Healthcare). They were obtained by separating PBMCs (Peripheral Blood Mononuclear cells). Collection of specimens containing human peripheral blood used in the study and the analysis were conducted in accordance with the Declaration of Helsinki, in accordance with the protocol that was approved by Mie University School of Medicine Research Ethics Committee with the written consent of the subjects.

Collected samples were stored in a refrigerator or a liquid nitrogen tank that had been encrypted not to identify the subjects and antitheft treatment. The personal information of the subjects was anonymous, and close attention were paid to personal privacy and the results of gene analysis so as not to be leaked to the outside.

9. mRNA Introduction into Cells by Electroporation
(1) Preparation of mRNA

DNA of CAR was cut into single stranded to produce a linear DNA template. DNA was purified using Wizard SV Gel and PCR Clean-UP System (Promega). mRNA was prepared from the purified DNA using mMESSAGEmMACHINE T7 Ultra Kit (Life technologies).

(2) Check by Bioanalyzer

Addition of Poly A to mRNA was confirmed by Bioanalyzer (Agilent Technologies).

(3) Preparation of PBMC Culture Plate

Anti-CD3 antibody (OKT-3 eBioscience) was diluted by ACD-A solution (TERUMO) at a final concentration of 5 µg/mL, RetroNectin (Takara Bio) was diluted by ACD-A solution at a final concentration of 25 µg/mL, 400 µL of two solutions were poured in each well of 12-well plate (Nunc), and incubated for 5-10 hours at 37° C. in $CO_2$ incubator.

(4) Preparation of CM (Culture Medium)

PBMC culture containing 50 mL of lymphocyte medium GT-T503, 50 µL of human IL-2 (600 IU), 400 µL of Albuminar(25% HSA), and 300 µL of plasma of lymphocytes donor was prepared.

(5) Isolation and Culture of PBMCs

Peripheral blood mononuclear cells were separated from healthy human blood (peripheral blood mononuclear cells, PBMCs) by Ficoll, and were suspended at $2 \times 10^5$ cells/mL by CM, 2.5 mL of the suspension was poured in plate, and cultured for 4 days at 37° C. in $CO_2$ incubator.

(6) Electroporation

The produced mRNA was introduced in PBMCs after 10 days from separation by electroporation. The introduced PBMCs were used in assay within 24 hours.

10. Gene Transfer into Cells by Retrovirus (Infection Experiment)
(1) Preparation of Retrovirus by Packaging Cell Plat-A CAR gene was introduced in packaging cell plat-A using FuGENE (Promega), after incubated for two days, the supernatant was recovered and used as virus solution.

(2) Isolation and Culture of PBMCs

Isolation and culture of PBMCs were carried out in accordance with above 9. (3)-(5).

(3) Production of plate for retrovirus infection

RetroNectin was diluted with ACD-A solution at a final concentration of 20 µg/mL. 500 µL of the solution was poured in each well of 24-well plate, and stored at 4° C. overnight. Before pouring virus solution, the plate was washed twice with ACD-A.

(4) Preparation of Retrovirus Plate for Infection, Infection to Cells

The virus solution prepared in above 10.(1) was poured in plate of retrovirus infection by 1 mL, the plate was centrifuged at 2000×g for 2 hours at 32° C. to coat the plate with virus. The plate was washed two times with 1.5% Alubuminar/PBS.

(5) Retrovirus Infection to PBMCs, Preparation of CAR-T Cells

PBMC cultured in above 10.(2) was recovered, after diluted by CM at $4 \times 10^5$, 950 µL of the suspension was seed on the plate for retrovirus infection, after the plate was centrifuged 1000×g for 10 minutes at 32° C., and incubated at 37° C. in CO2 incubator.

Prepared CAR-T cell was used in assay after 12-14 days from PBMCs separation.

(6) Preparation of Control Cell

Part of cultured cells in above 10.(2) was used as a control cells (no operation of gene transfection).

11. Characteristics of Tumor Cell Lines Used in In Vitro Experiments

Characteristics of the cell lines used in in vitro experiments were shown in Table 4.

TABLE 4

| Cell line | A2 | A24 | MAGE-A4 |
| --- | --- | --- | --- |
| NW-MEL-38 | + | − | 6.01E+03 (+) |
| LB-23 | + | + | 1.95E+03 (+) |
| LC-1/sq | − | + | 1.61E+03 (+) |
| MEL72 | + | + | 4.00E−01 (−) |
| HCT116 | + | − | − |
| T2 | + | − | − |
| SK-MEL-37 | + | − | + |

12. IF-γ Release Assay

The concentration of IF-γ in culture was determined using eBioscience kit by ELISA.

10×Coating buffer was diluted 10-fold with purified water to prepare Coating buffer. 48 µL of the primary antibody was added to 12 mL of Coating buffer. The buffer was added to 96 well-flat-bottom-plate by 100 µL per well. After the plate was stored at the 4° C. overnight, it was washed five times with 0.05% PBS-T. 5×Assay diluents was diluted 5-fold with purified water to prepare Assay diluents. Assay diluents was added by 200 µL per well. After 1 hour at room temperature for blocking, the plate was washed 5 times with 0.05% PBS-T. IFN-γ was prepared at 1000 pg/mL with maxima, it was diluted with 7 stages by two folds to prepare standards. Samples and standards were added to the plate and reacted for 2 hours at room temperature, and the plate was washed 5 times with 0.05% PBS-T. 48 µL of the secondary antibody was added to 12 mL of Assay diluents, the diluents was added by 100 µL per well. After the plate was stored for 1 hour at room temperature, it was washed five times with 0.05% PBS-T. 48 µL of Streptavidin-HRP was added to 12 mL of Assay diluents, the solution was added by 100 µL per well. The plate was reacted in dark for 30 minutes at room temperature, and washed seven times with 0.05% PBS-T. TMB Substrate solution was added by 100 µL, reacting in dark for 15 minutes at room temperature, 50 µL of 0.18M $H_2SO_4$ was added to stop the reaction. Immediately, the plate was measured at a wavelength of 450 nm with Microplate Reader Model 680 (Bio-Rad).

13. Intracellular Cytokine Staining (ICS)

Target cells were adjusted to $1\times10^5$ cells/mL, the effector cells were adjusted to $1\times10^5$ cells/mL. 0.5 µL of APC Anti human CD107a per sample was added, target cells and effector cells were added at the ratio of 1:1 in 96-well plate (U), was co-cultured for 1 hour at 37° C. Then, 0.7 µL of Golgistop (Protein Transport Inhibitor) was added for each well, and incubated for 4 hours at 37° C. The cells in each well were transferred to V-type 96-well plate, after centrifuged at 1200 rpm for 5 minutes at 4° C., then washed twice with 0.5% BSA/PBS. 0.5 µL of APC-cy7 anti-human CD4 and 0.5 µL of FITC anti-human CD8 were added to each well, and stood on ice for 20 minutes in dark, and the plate was washed twice with 0.5% BSA/PBS. 100 µL of cell fixative solution (Cytofix/Cytoperm: BD) was added, stood on ice for 20 minutes in dark, 100 µL of perm/wash (BD) was added and centrifuged. Then, the plate was washed two times with perm/wash solution. 0.5 µL of V450 IFN-γ and 0.5 µL of PE-Cy7 TNF-α were added to each well. Under dark conditions, the plate was stood on ice for 30 minutes, washed twice with 0.5% BSA/PBS. Thereafter, the plate was measured by FACSCanto II flow cytometer (BD), and data was analyzed by FACS Diva Software (BD).

14. Long Peptide Uptake by APC, Cross Presentation
(1) MAGE-A4 Long Peptide

The amino acid sequence of MAGE-A4 long peptide was NYKRCFPVIF GKASEGVYDG REHTVYGEPR KAETSYVKVL EHVVRVNARV RI (SEQ ID NO: 28), the molecular weight of the peptide was 6006.811. The long peptide was designed by connecting A24 MAGE-A4 143-151 epitope (NYKRCFPVI: SEQ ID NO: 29), A2 MAGE-A4 230-239 epitope (GVYDGREHTV: SEQ ID NO: 1) and a helper epitope (AETSYVKVLE HVVRVNARVR I: SEQ ID NO: 30).

(2) CHP-Long Peptides

CHP-long peptide means an object that MAGE-A4 long peptide was wrapped in CHP nanogel as a drug delivery system. Cellular immunity induction can be expected by using the object (Non-patent document 5).

(3) CD3 Negative Beads Selection $1\times10^7$ cells of human lymphocytes were suspended in 80 µL of 2% FCS/PBS. To the suspension, 20 µL of CD3 Micro Beads (Miltenyi Biotec) was added, and mixed well. After 15 minutes at 4° C. in light shielding, the suspension was washed with 10 volumes of 2% FCS/PBS. Cells were suspended in 3 mL of 2% FCS/PBS to use as cell suspension. The cell suspension was applied to MACS Separator equipped with a MACS column. Fractions that was passed through the column was CD3-negative fractions, used as APC.

15. Assay Cytotoxicity
(1) Cr Release Assay

After target cells were collected by centrifugation, they were suspended in 100% FCS at a final concentration of $1\times10^6$ cells/50 µL. Thereto, 50 µCi ($3.7\times10^6$ Bq) of $^{51}$Cr was added, and incubated for 1 hour at 37° C. in $CO_2$ incubator. The concentration of effector cells were adjusted according to the E/Tratio by 10% FCS-RPMI1640, and were seeded in U-shaped 96-well plate. After cultivation, cells were washed three times with 10% FCS-RPMI1640. Cells were suspended in 10% FCS-RPMI1640 at a final concentration of $1\times10^5$ cells/mL, were seed at $1\times10^4$ cells/100 µL/well in U-shaped 96-well plate, and were cultured for 8 hours in CO2 incubator at 37° C. After cultivation, the plate was centrifuged at 1200 rpm for 5 minutes at 4° C., 30 µL of supernatant was transferred to the plate for reading, and dried up by air drying overnight. The amount of $^{51}$Cr was determined by scintillation counter MicroBeta2 (Perkin Elmer). Calculation of the cytotoxic activity was determined by the following equation. The maximum release value was the measured value when 100 µL of 1% NP-40 was added.

Cytotoxic activity (%)=100×(measured value (cpm)−spontaneous release value (cpm))/(maximum release value (cpm)−spontaneous release value (cpm))

16. In Vivo Cancer Treatment Model Experiment Using NOG Mouse
(1) Used Mice

NOG mice (NOD/Shi-scid, IL-2RyKO Jic) was purchased from CLEA Japan, Inc. The female mice were used in the experiment at 7-8 weeks of age. T cell infusion therapy with laboratory animals and the study of gene immunotherapy were approved by the recombinant DNA experiment committee of Mie University, Mie University School of Medicine Research Ethics Committee, and the animal research committee. The mice were bred in Mie University Life Science Center for the Research and Support of Animal Research Facility.

(2) Implantation of Human Tumor and Total Body Irradiation (TBI)

As pretreatment, total body irradiation (TBI) with 2.5Gy to NOG mice was conducted the day before cell infusion. The number of lymphocytes in recipient was reduced by the pretreatment, for transfused donor lymphocytes to be engrafted easily. CAR-T cells and human lymphocytes for infusion were $1\times10^7$ cells/animal. Cells were transfused from the tail vein of NOG mice. Body weight was measured every 2-3 days.

Tumor transplantation into NOG mice were carried out in 7 days prior to infusion of the CAR-T cells, NW-MEL-38 (A2-positive MAGE-A4-positive) by $2.5\times10^6$ cells/mouse were injected in the right-side of mouse, HCT116 (A2-positive MAGE-A4-negative) by $2.5\times10^6$ cells/mouse were injected subcutaneously in the left side of mouse. Tumor diameters were measured every 2-3 days.

(3) Preparation of Cells for Infusion

CAR-T cells for infusion were prepared according to the method of above "10. Gene transfer into cells by retrovirus".

(4) PBMCs Isolation in Mouse Peripheral Blood by Orbital Blood Sampling

Peripheral blood was collected from the orbital of mouse, PBMCs were separated using Ficoll. They were stained with A2-MAGE-A4 tetramer, human CD4CD8 fluorescent antibody, infused cells were confirmed by FACS.

(5) Confirmation of TIL (Tumor Infiltrating Lymphocytes)

Tumor taken from mouse was mashed, stained with A2-MAGE-A4 tetramer human CD4CD8 fluorescent antibody, and transfused cells were confirmed by FACS.

(6) Immunostaining

Tumor excised from mouse was frozen in liquid nitrogen, frozen sections were prepared by cryostat. These sections ware stained by DAPI, human CD4-FITC and human CD8-FITC, and observed with a fluorescence microscope.

Figure 21:
FIG. 21 shows the gene sequence image of CAR zG.

17. In Vitro Experiments with zG-Type-CAR-Introduced-CD8-Positive T Cells and 4-1BBz-Type-CAR-Introduced-CD8-Positive T Cells The effects of CAR-T cells due to differences of ICD region were confirmed. Specifically, GITR (zG) type and CD137 (4-1BBz) type CAR were produced from CD28 (28z) type CAR, the effects of them were confirmed. As shown in FIG. 21, GITR (glucocorticoid-induced tumor necrosis factor receptor) was used instead of CD28 as ICD in CAR zG. Similarly, CD137 (4-1BBz) was used instead of CD28

As a control, CAR-untransfected-CD8-positive T cells (NGMC) was used.

<Results>
1. Isolation and Evaluation of Antibody that Recognizes HLA-A2-MAGE-A4

Figure 3:
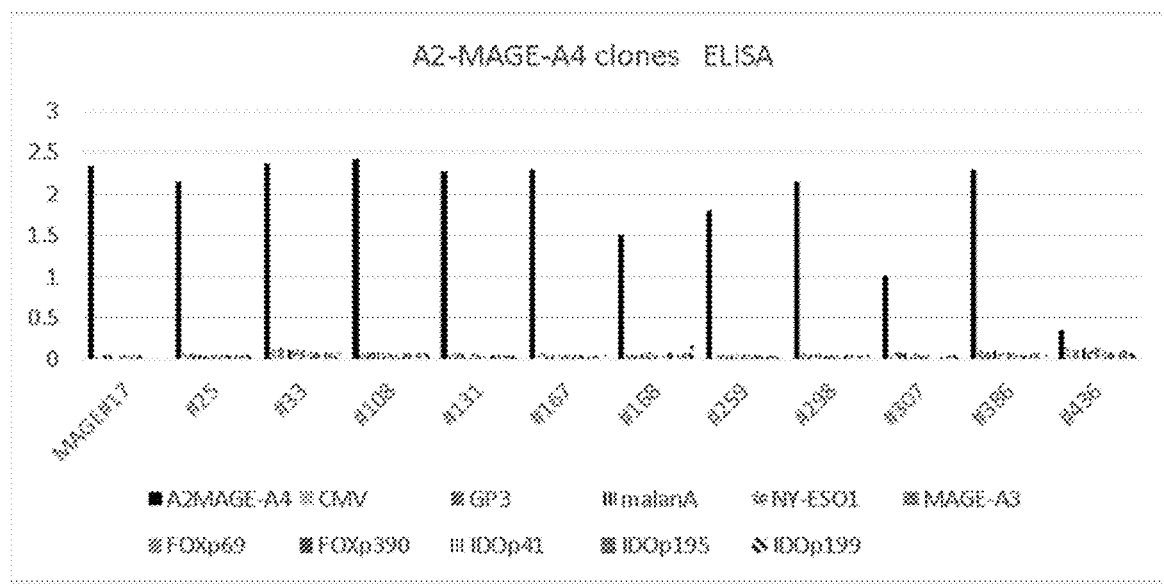
FIGS. 3(A) and 3(B) show bar graphs illustrating the results of reactivity of picked-up-clones to multiple antigens evaluated by ELISA.
Figure 3:
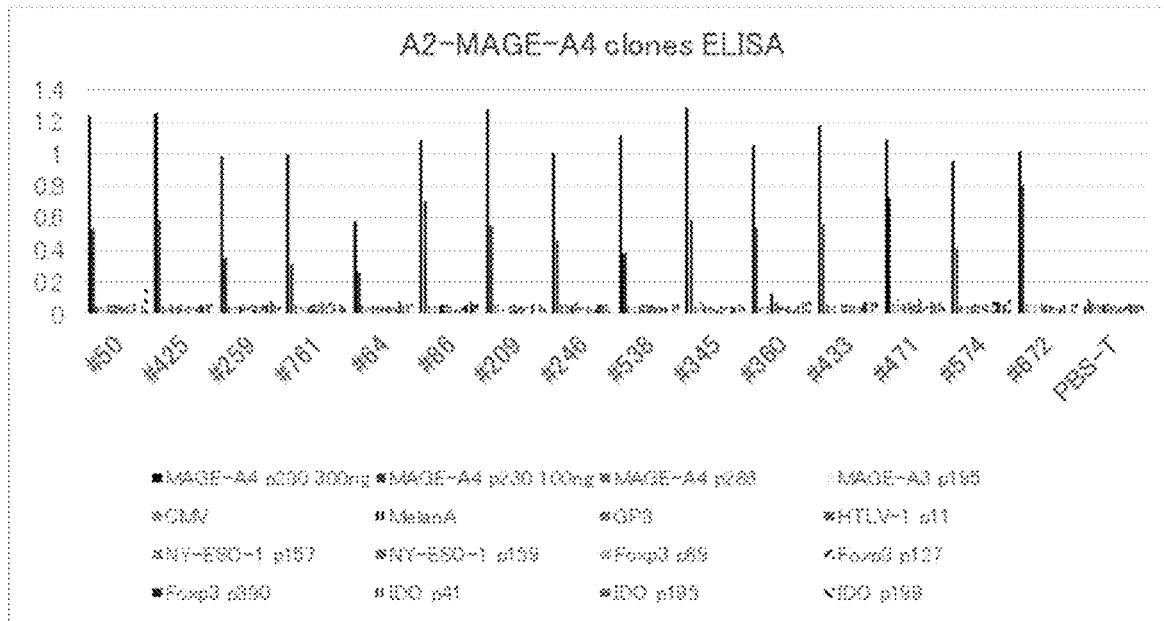

MAGE-A4 (HLA-A2-MAGE-A4) is known to be highly expressed in melanoma. Therefore, a plurality of antibodies that recognize MAGE-A4 were isolated by screening using human antibody libraries. Phage display method was used for isolation of antibodies. In the method, scFv is presented as part of a phage coat protein cp3, clones that bind to antigen with high affinity can be selected by ELISA. After picked up about 1500 clones, ELISA was conducted in the state of scFv-CP3. The clones that responded to HLA-A2-MAGE-A4 as a positive target and did not respond to A2-CMV as a negative target were selected. To examine the binding specificity of the selected antibodies, ELISA was conducted using plural peptides-MHC complex (pMHC). Each pMHC monomer, containing HLA-A2-MAGE-A4 p230, MAGE-A4 p286, MAGE-A3 p195, CMV, MelanA, GP3, HTLV-1 p11, NY-ESO-1 p157, NY-ESO-1 p159, Foxp3 p69, Foxp3 p127, Foxp3 p390, IDO p41, IDO p41, IDO p195 and IDO p199 were immobilized, ELISA was conducted using selected antibodies. Some results of the ELISA were shown in FIG. 3.

Fifteen clones exhibiting a specific reaction to HLA-A2-MAGE-A4 were obtained after compared the sequence of the clones showing strong binding to HLA-A2-MAGE-A4. Among them, 5 clones showing strong binding, i.e. MAGE #17, #86, #209, #345 and #672, were selected as candidate clones and proceeded analytics.

Figure 4:
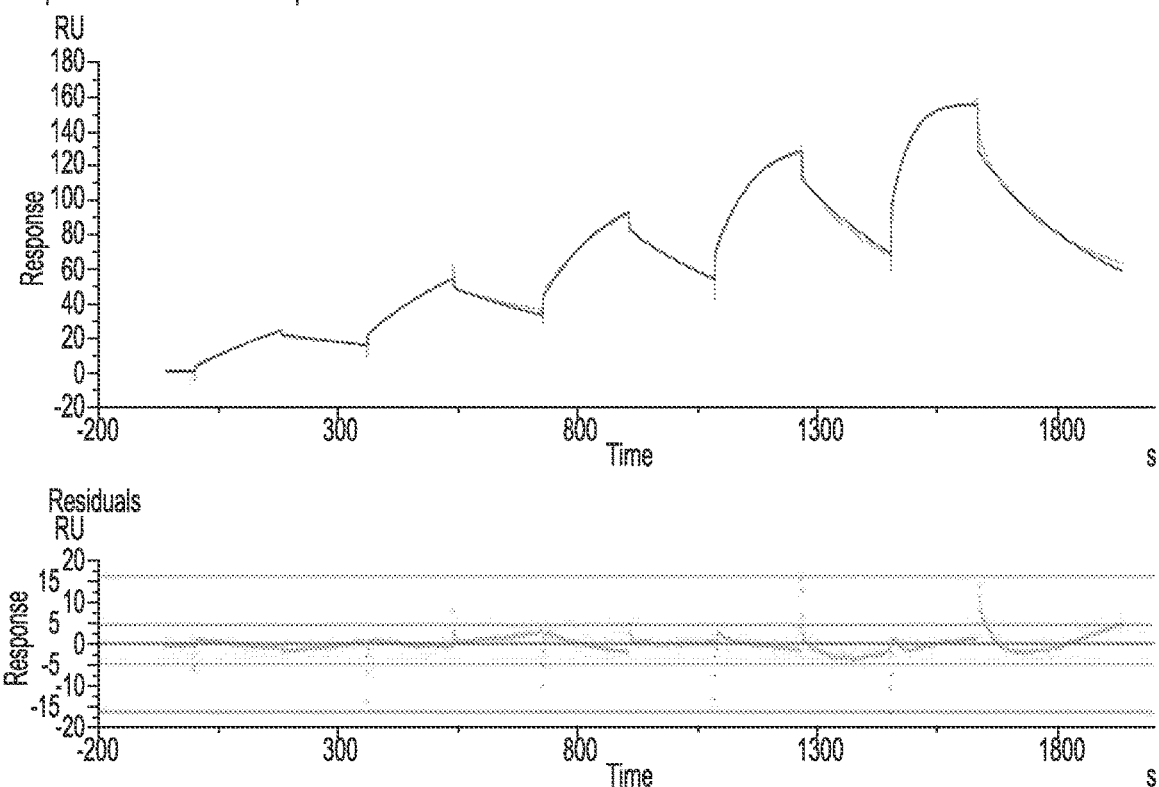

Next, KD value of MAGE #17 antibody was measured with BiacoreX100. Determination of KD value by Biacore was determined by measuring the dynamic changes in detection sensitivity (resonance, reflecting the change in mass on the chip) over time. The dissociation rate constant (Kd) and the binding rate constant (Ka) were determined by dynamic change curve, the binding constant was determined from the ratio of the two constants. As a result of the measurement, the binding constant of MAGE #17 was 22 nM (FIG. 4).

2. Study Concerning Recognition Specificity to the A2-MAGE-A4 Complex and Risk Antigen of the Obtained Antibodies T2 cell lacks Transporter Associated with Antigen Processing (TAP), does not present the intracellular protein to HLA. When peptide was pulsed to T2 cell, as HLA was stabilized on T2, HLA expression level was confirmed by using fluorescent-anti-HLA antibody, it can be recognized what extent of peptide binds to HLA.

Figure 5:
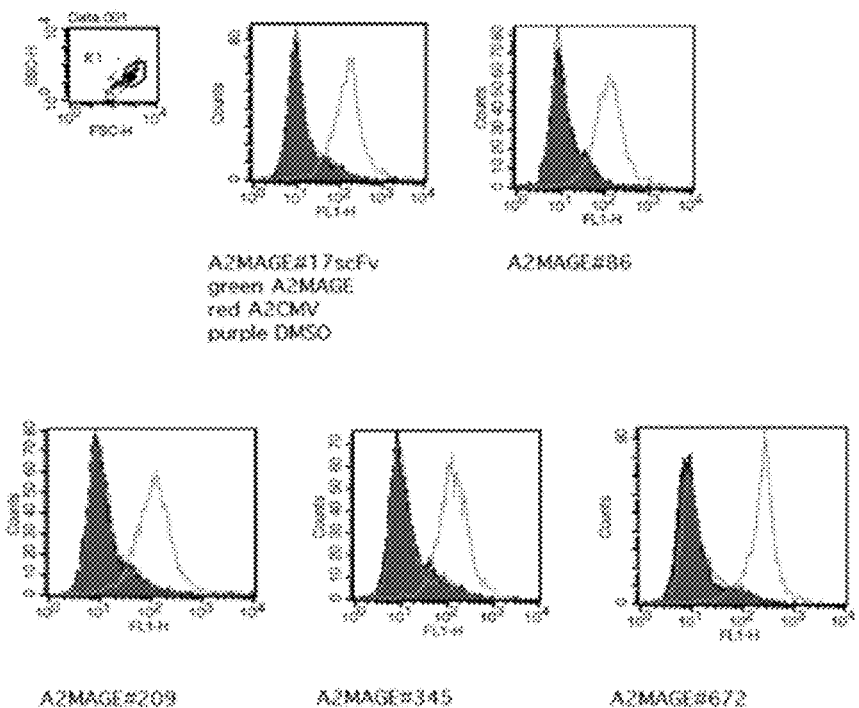
FIG. 5(A) shows graphs of the results of examining the shift amounts obtained by reacting antibodies MAGE #17, #86, #209, #345 and #672 to T2 cells pulsed with MAGE-A4p230, CMV, and DMSO.
FIG. 5(B) shows bar graph of the results.
Figure 5:
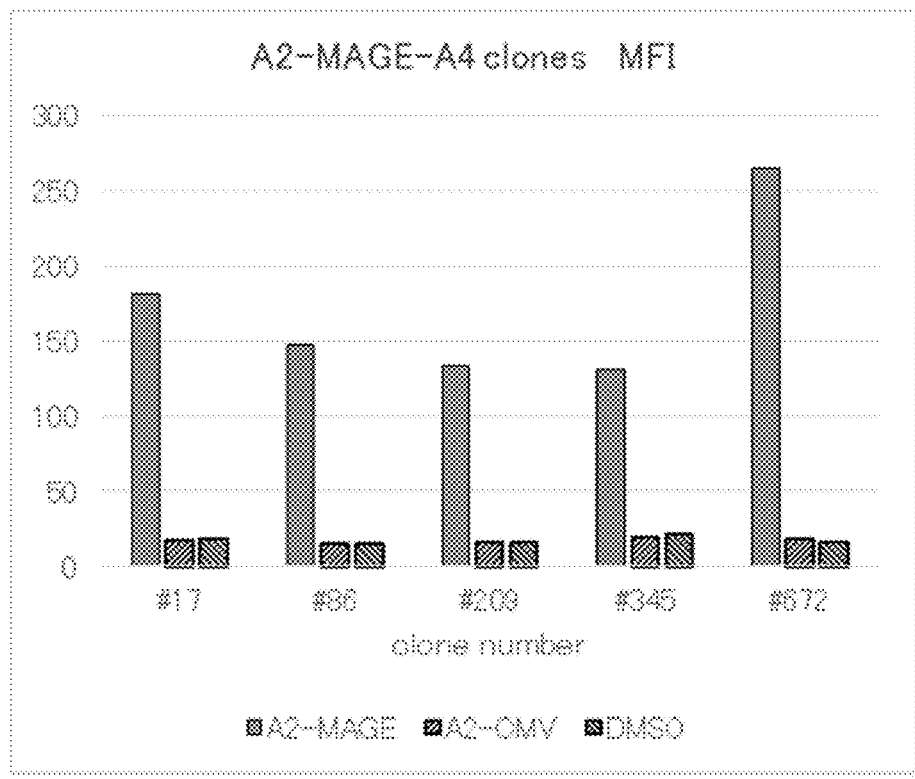

Selected antibodies, i.e. anti-MAGE #17, #86, #209, #345, and #672 were reacted with T2 cells pulsed with MAGE-A4p230, CMV, and DMSO, the shift amount was determined by FACS. Only in T2 cell pulsed with MAGE-A4 p230, selected antibody clones, MAGE #17, #86, #209, #345, and #672 showed the change in the shift amount (FIG. 5).

Figure 6:
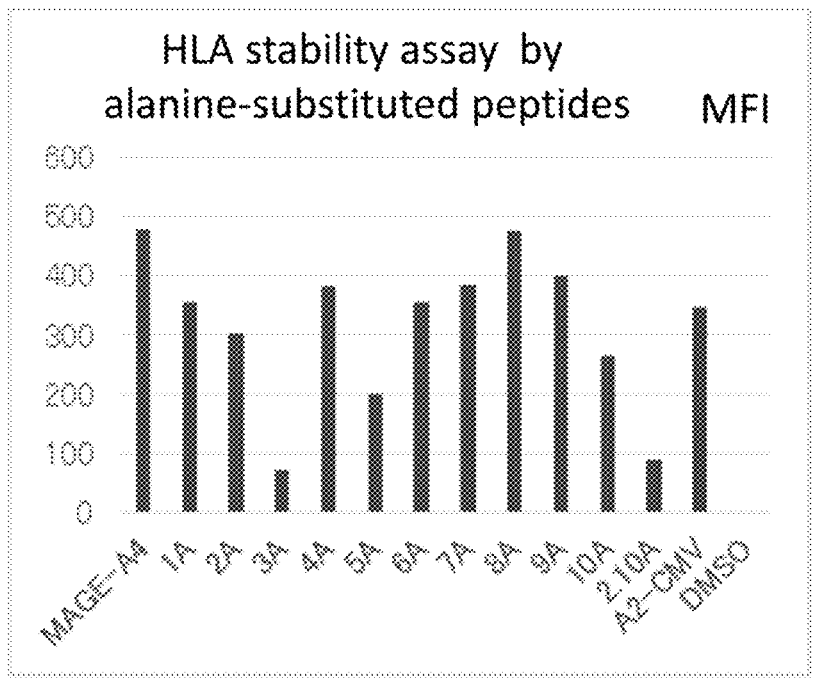
FIG. 6 shows a graph of the results of examining the HLA amounts on the surface of T2 cells pulsed with the alanine-substituted peptides measured by FACS.

Next, in order to search for amino acids that correlated the recognition of antibodies, peptides with one amino acid substitution by another amino acid (mainly alanine) of MAGE-A4 p230 (GVYDGREHTV: SEQ ID NO: 1) were prepared, the binding force between HLA-A*0201 and the peptide was examined using IEDB (Immune Epitope Database), and determined MHC IC50 (Table 2). MHC IC50 is the theoretical value calculated by the IEDB, when the value is lower, the bond with HLA-A* 0201 and the peptide is stronger. Alanine substituted peptides were pulsed to T2 cell, the amount of HLA on the surface of T2 cell were determined by FACS (FIG. 6). More strongly a peptide bind to HLA, the structure of peptide-HLA was stabilized, since the shift amount of FACS was increased, the value of MFI was an indicator of binding strength of the peptide and HLA. Except some of the peptides, the MFI value and the MHC IC50 value corresponded to each other.

Figure 7:
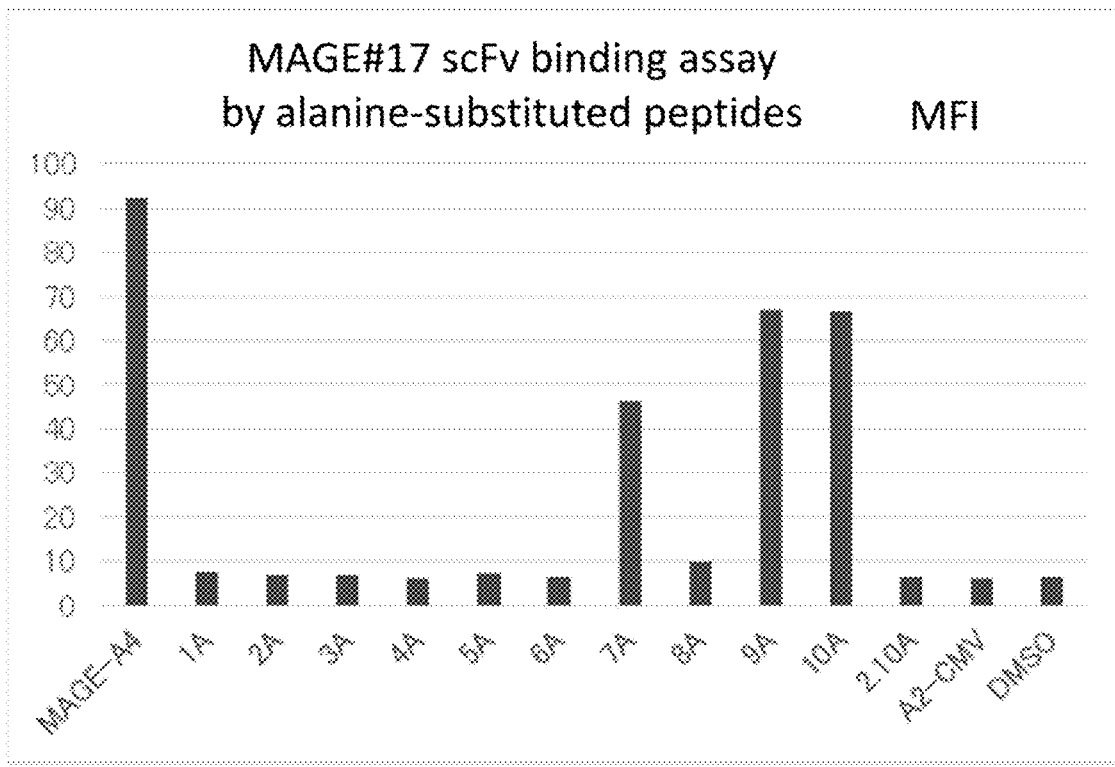
FIG. 7 shows a graph of the results of examining the amino acid related to antibody recognition by reacting MAGE #17 to T2 cells pulsed with the alanine-substituted peptides.
Figure 8:
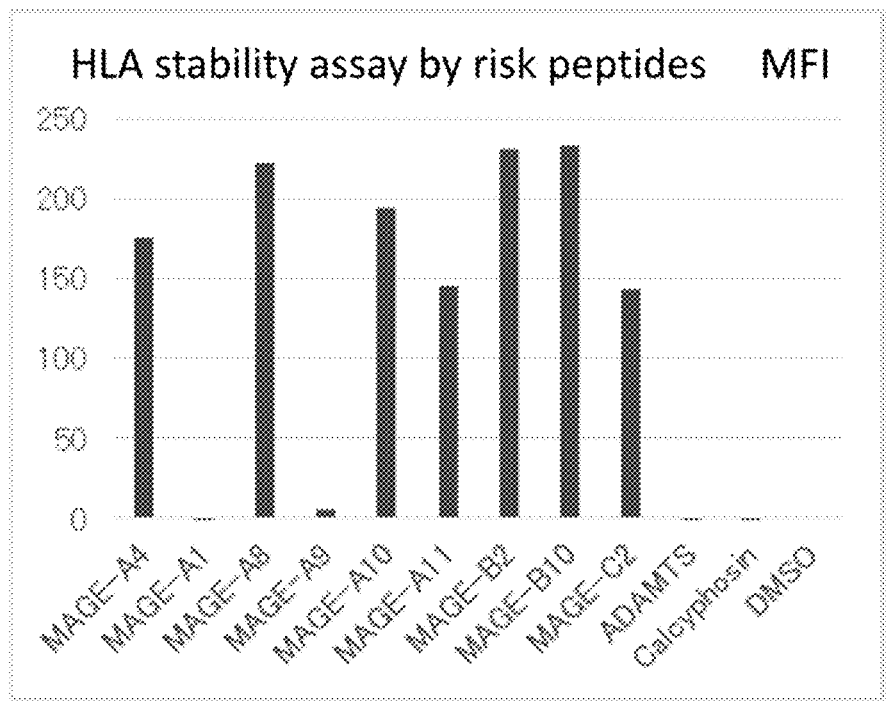
FIG. 8 shows a graph of the results of examining the HLA amounts of the surface of T2 cells pulsed with risk peptides measured by FACS.

Then, alanine-substituted peptide was pulsed to T2 cell, and reacted with MAGE #17, amino acid involved in the recognition of the antibody was examined (FIG. 7). Since the MFI value dropped with 1A, 2A, 3A, 4A, 5A, 6A, and 8A, the seven amino acids were determined to be involved in the recognition. The amino acid sequence of GVYDGRxHxx was conducted by BLAST search, risk peptide was extracted (Table 3). After T2 cell was pulsed by risk peptide, the amount of HLA on the surface of T2 cell was determined by FACS. Similar to the results shown in FIG. 6, the MFI value and the MHC IC50 value of MFI corresponded to each other (FIG. 8).

Figure 9:
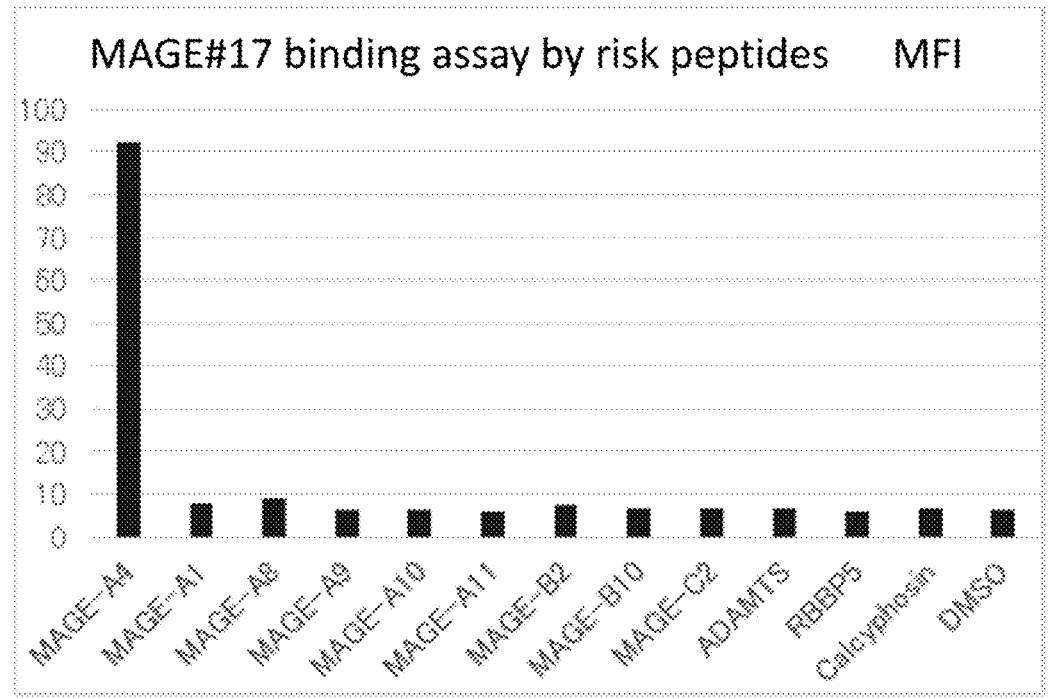
FIG. 9 shows a graph of the results of examining the reactivity with the risk peptides by reacting MAGE #17 to T2 cells pulsed with the risk peptides.

Then, T2 cell was pulsed by risk peptide, reacted with MAGE #17, and confirmed that the T2 cell does not recognize the risk peptide (FIG. 9). Similar assays were practiced using other clones #86, #209, #345, and #672, in the results, clone #17 had most amino acids involved in the antigen recognition. For this reason, MAGE #17 was made as the final candidate.

```
Nucleotide sequence (SEQ ID NO: 31) and amino
acid sequence (SEQ ID NO: 32) of MAGE #17
were shown. Nucleotide sequence of MAGE #17
(SEQ ID NO: 31):
CAGGTCCAGC TGGTACAGTC TGGGGCTGAG GTGAAGAAGC

CTGGGTCCTC GGTGAAGGTC TCCTGCAAGG CTTCTGGAGG

CACCTTCAGC AGCTATGCTA TCAGCTGGGT GCGACAGGCC

CCTGGACAAG GGCTTGAGTG GATGGGAGGG ATCATCCCTA

TCTTTGGTAC AGCAAACTAC GCACAGAAGT TCCAGGGCAG

AGTCACGATT ACCGCGGACA AATCCACGAG CACAGCCTAC

ATGGAGCTGA GCAGCCTGAG ATCTGAGGAC ACGGCCGTGT

ATTACTGTGC GAGATCCCCC CGGCGGGCAT ATCATGATGC

TTTTGATATC TGGGGCCAAG GGACAATGGT CACCGTCTCT

TCAGGTGGAG GCGGTTCAGG CGGAGGTGGC AGCGGCGGTG

GCGGGAGTTC CTATGAGCTG ACTCAGCCAC CCTCGATGTC

AGTGGCCCCA GGAAAGACGG CCAGCATTAC CTGTGGCGGA

GACCATATTG GAAGTAAAAG TGTTCACTGG TACCAGCAGA

AGCCAGGCCA GGCCCCTGTA CTGGTCGTCT ATGATGATAG
```

```
                           -continued
CGACCGGCCC TCAGGGATCC CTGAGCGATT CTCTGGCTCC

AACTCTGGGA ACACAGCCAC TCTGACCATC AGCGGGACCC

AGGCTATGGA TGAGGCTGAC TATTACTGTC TGGCGTGGGA

CAGCAGCACT GCGATCTTCG GCGGAGGGAC CAAGCTGACC

GTCCTC.
The amino acid sequence of MAGE #17
(SEQ ID NO: 32):
QVQLVQSGAE VKKPGSSVKV SCKASGGTFS SYAISWVRQA

PGQGLEWMGG IIPIFGTANY AQKFQGRVTI TADKSTSTAY

MELSSLRSED TAVYYCARSP RRAYHDAFDI WGQGTMVTVS

SGGGGSGGGG SGGGGSSYEL TQPPSMSVAP GKTASITCGG

DHIGSKSVHW YQQKPGQAPV LVVYDDSDRP SGIPERFSGS

NSGNTATLTI SGTQAMDEAD YYCLAWDSST AIFGGGTKLT

VL.

The above sequences show that the nucleotide
sequence contains VH (SEQ ID NO: 33), sc
(SEQ ID NO: 34) and VL (SEQ ID NO: 35), and
the amino acid sequence contains VH
(SEQ ID NO: 36), sc (SEQ ID NO: 37) and VL
(SEQ ID NO: 38), as shown in following.

The nucleotide sequence of VH
(SEQ ID NO 33): CAGGTCCAGC
TGGTACAGTC TGGGGCTGAG GTGAAGAAGC CTGGGTCCTC

GGTGAAGGTC TCCTGCAAGG CTTCTGGAGG CACCTTCAGC

AGCTATGCTA TCAGCTGGGT GCGACAGGCC CCTGGACAAG

GGCTTGAGTG GATGGGAGGG ATCATCCCTA TCTTTGGTAC

AGCAAACTAC GCACAGAAGT TCCAGGGCAG AGTCACGATT

ACCGCGGACA AATCCACGAG CACAGCCTAC ATGGAGCTGA

GCAGCCTGAG ATCTGAGGAC ACGGCCGTGT ATTACTGTGC

GAGATCCCCC CGGCGGGCAT ATCATGATGC TTTTGATATC

TGGGGCCAAG GGACAATGGT CACCGTCTCT TCA.

The nucleotide sequence of sc region
(SEQ ID NO 34):
GGTGGAGGCG GTTCAGGCGG AGGTGGCAGC GGCGGTGGCG

GGAGTTCCTA T.

The nucleotide sequence of the VL region
(SEQ ID NO 35):
GAGCTGACTC AGCCACCCTC GATGTCAGTG GCCCCAGGAA

AGACGGCCAG CATTACCTGT GGCGGAGACC ATATTGGAAG

TAAAAGTGTT CACTGGTACC AGCAGAAGCC AGGCCAGGCC

CCTGTACTGG TCGTCTATGA TGATAGCGAC CGGCCCTCAG

GGATCCCTGA GCGATTCTCT GGCTCCAACT CTGGGAACAC

AGCCACTCTG ACCATCAGCG GGACCCAGGC TATGGATGAG

GCTGACTATT ACTGTCTGGC GTGGGACAGC AGCACTGCGA

TCTTCGGCGG AGGGACCAAG CTGACCGTCC TC.
                           -continued
The amino acid sequence of VH region
(SEQ ID NO: 36):
QVQLVQSGAE VKKPGSSVKV SCKASGGTFS SYAISWVRQA

PGQGLEWMGG IIPIFGTANY AQKFQGRVTI TADKSTSTAY

MELSSLRSED TAVYYCARSP RRAYHDAFDI WGQGTMVTVS S.

The amino acid sequence of sc region
(SEQ ID NO: 37):
GGGGSGGGGS GGGGSSY.

The amino acid sequence of VL region
(SEQ ID NO: 38):
ELTQPPSMSV APGKTASITC GGDHIGSKSV HWYQQKPGQA

PVLVVYDDSD RPSGIPERFS GSNSGNTATL TISGTQAMDE

ADYYCLAWDS STAIFGGGTK LTVL.
```

Figure 10:
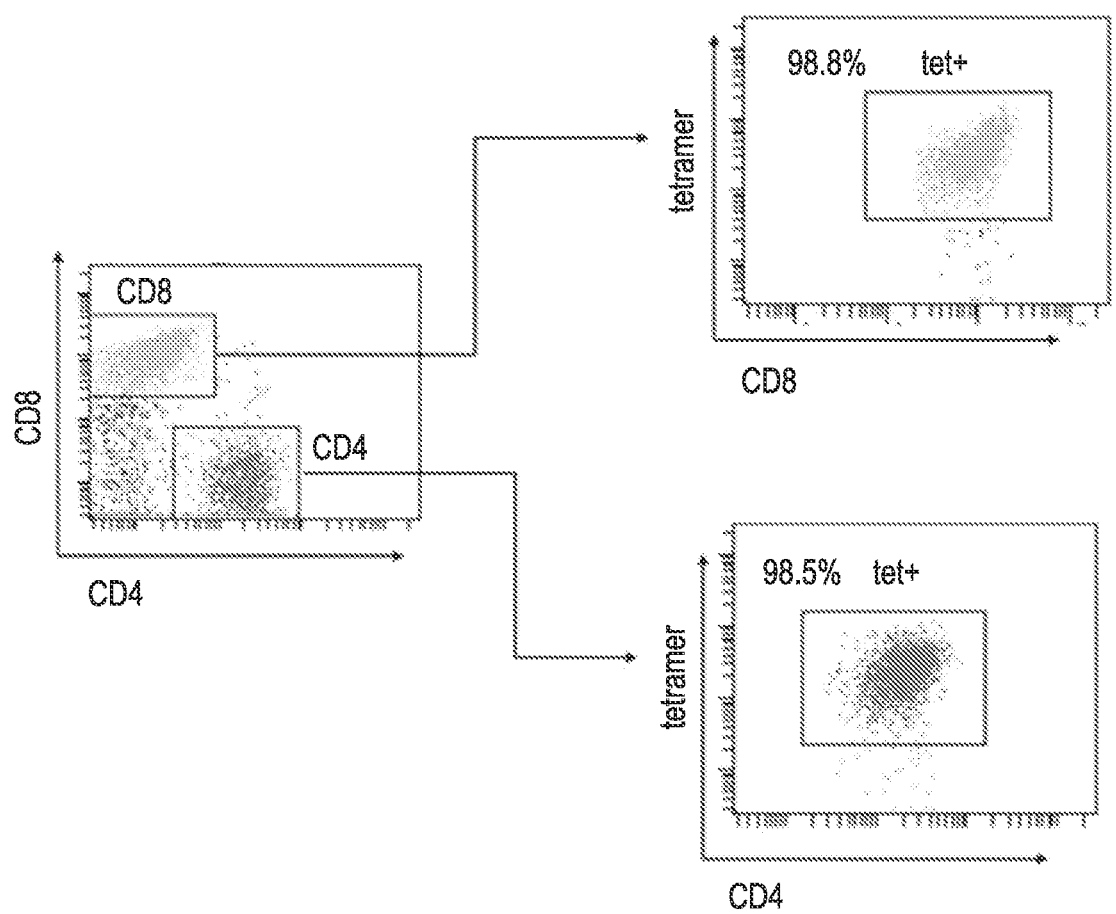
FIG. 10 shows the results of examining whether CAR (mRNA) introduced to PBMCs was expressed or not, by tetramer staining.
Figure 11:
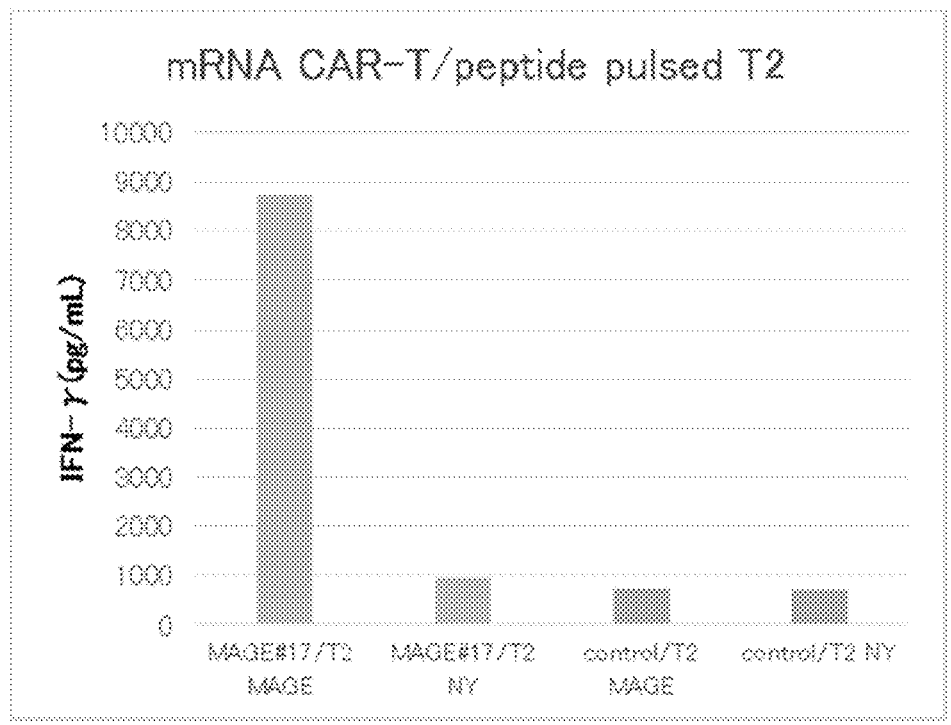
FIGS. 11(A) and 11(B) show graphs of the results that CAR-T cells transfected with mRNA recognize target cells specifically, and increase IFNγ production.
Figure 11:
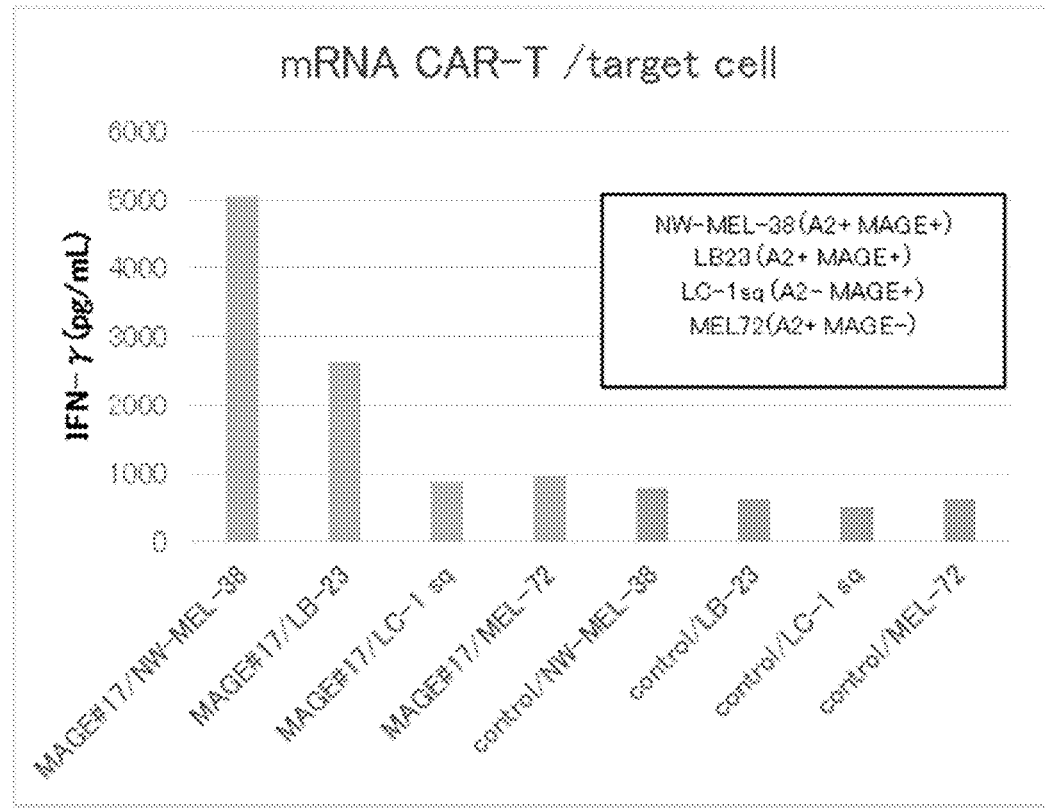

3. MAGE #17 CAR Specifically Recognizes Target Cancer Cells and the Production of IFN-γ was Increased Since the specificity of the antibody clone MAGE #17 was confirmed, MAGE #17 was replaced to the vector of CAR. Then, after preparing mRNA, it was confirmed by bioanalyzer, CAR gene was introduced to human peripheral blood lymphocytes (PBMCs) by electroporation method. Whether or not the introduced CAR expressed normally was confirmed by tetramer staining. Consequently, CAR positive rate of CAR-T cells was 98.8% by CD8, and was 98.5% by CD4 (FIG. 10). CAR-T cell and peptide-pulsed T2 cell were co-cultured for 24 hours, and IFN-γ in the culture supernatant was measured, production of IFN-γ in T2 cell pulsed with MAGE-A4 was specifically increased. Similar assay was conducted using control cells (cells with no gene transfection). Further, tumor-specific production of IFN-γ was observed in target cells of A2 positive MAGE-A4-positive NW-MEL-38 and LB-23, as compared with off-target cells of LC-1/sq and MEL72 (FIG. 11).

Figure 12:
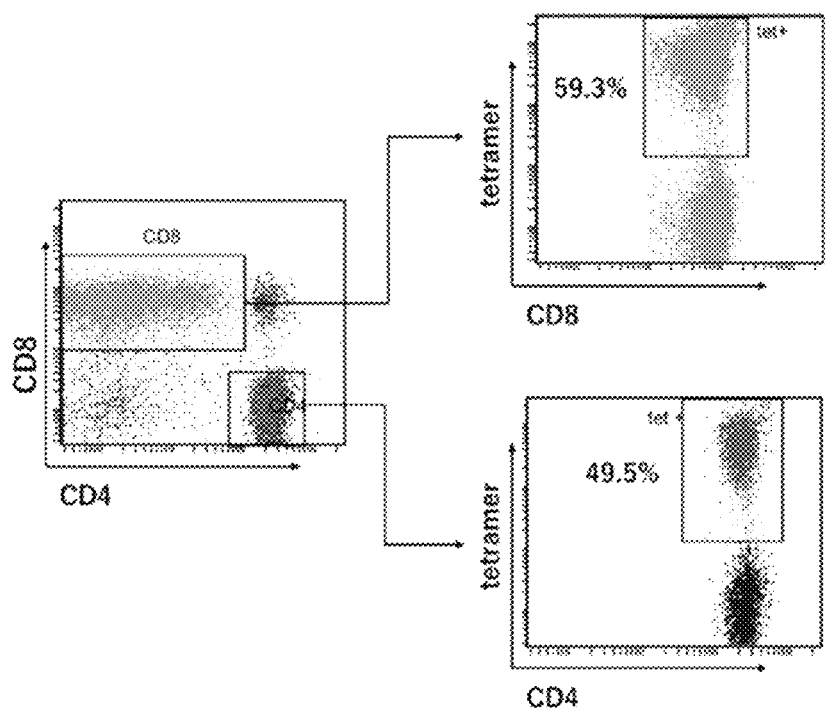
FIG. 12 shows the results of examining whether CAR gene (retrovirus) introduced to PBMCs was examined or not, by tetramer staining.

Since the expression of CAR by mRNA was transient, gene transfection by retrovirus was conducted for permanent expression of CAR. After a retrovirus vector was constructed for CAR introduction, the retrovirus was prepared by packaging cells plat-A, CAR-T cell was produced by infecting the retrovirus to PBMCs. Gene transfer was conducted according to the method of the above section 10 (Gene transfer into cells by retrovirus). The expression of CAR was confirmed by tetramer staining. Consequently, the CAR positive rate of CAR-T cells was 59.3% by CD8, and was 49.5% by CD4 (FIG. 12).

Figure 13:
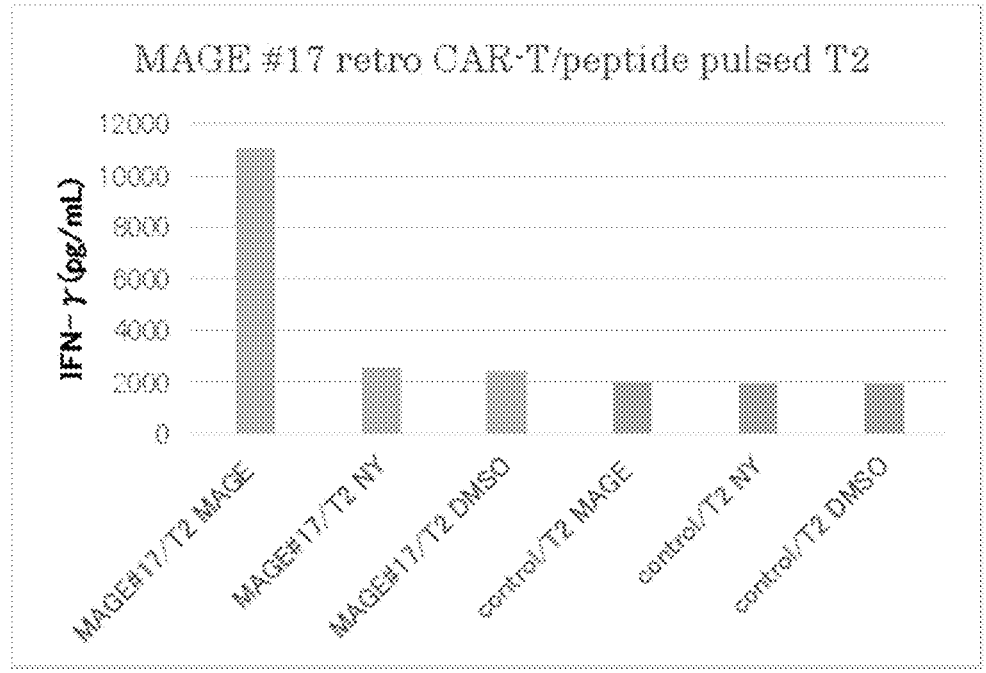
FIGS. 13(A) and 13(B) are graphs showing that CAR-T cells transfected with retrovirus specifically recognize the target cells, and increase IFNγ production.
Figure 13:
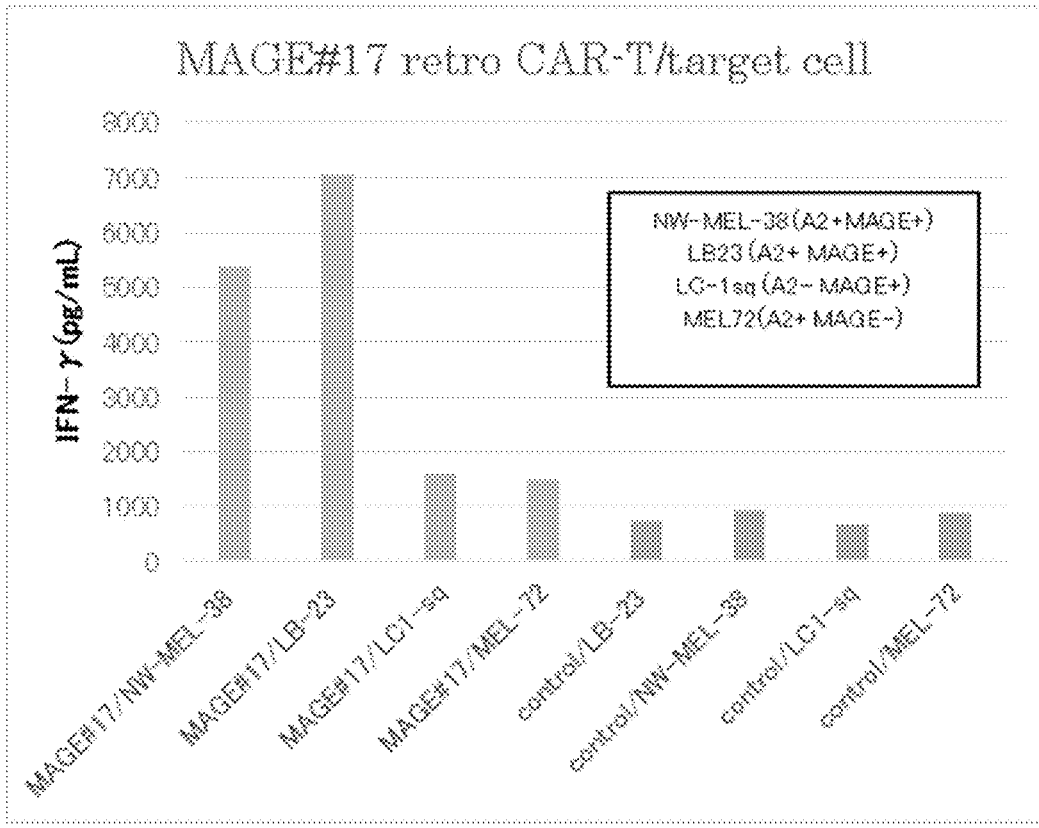

Gene-transferred CAR-T cells by retrovirus and peptide-pulsed T2 cells were co-cultured for 24 hours, IFN-γ in the culture supernatant was measured, production of IFN-γ in T2 cell pulsed with MAGE-A4 was specifically increased. Similar assay was conducted using control cells (cells with no gene transfection). Further, tumor-specific production of IFN-γ was observed in target cells of A2 positive MAGE-A4-positive NW-MEL-38 and LB-23, as compared with off-target cells of LC-1/sq and MEL72 (FIG. 13). It was confirmed that CAR was expressed by introduction of mRNA and introduction of CAR gene by retrovirus vectors, the cell specifically recognized tumor, and produced IFN-γ.

4. CAR-T Cell Introduced with MAGE #17 CAR Gene Specifically Recognized Target Cancer Cells and Showed Cytotoxic Activity The CAR-T cell was expected to recognize A2-MAGE-A4 expressed as antigen on cancer cells, become activated and exhibit cytotoxic activity. IFN-γ, TNF-α and CD107a are known indicators of T cell activation, i.e. they are expressed increasingly according to the activation of T cell.

Therefore, intracellular cytokine staining (intracellular cytokine staining: ICS) of peptide-pulsed T2 cell and MAGE #17 CAR co-cultured with target cells was conducted.

Figure 14:
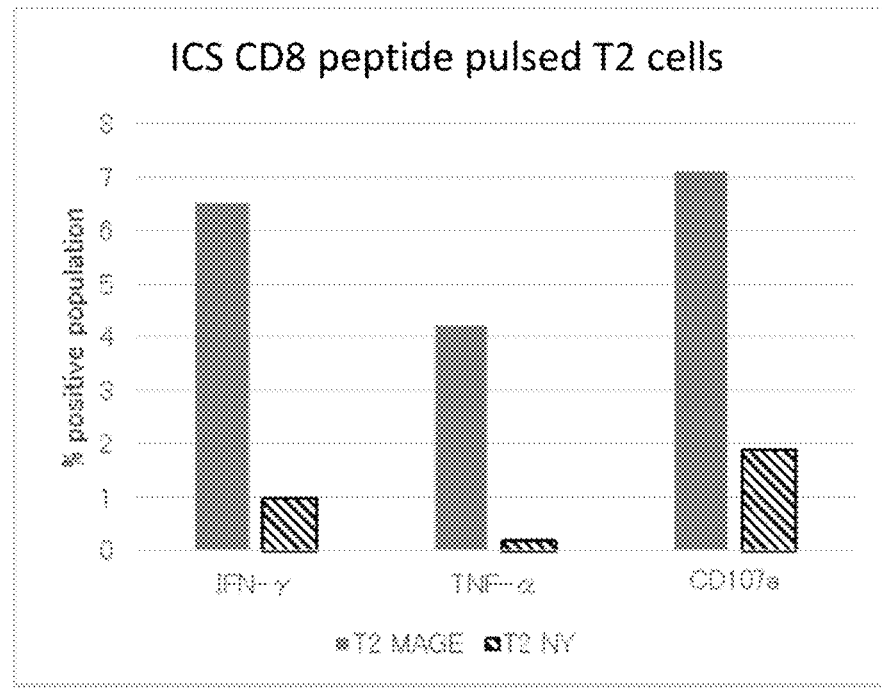
FIG. 14 is a graph showing that T cells transfected with MAGE #17 CAR were activated by co-culture with T2 cells pulsed with the MAGE-A4 peptide.
Figure 15:
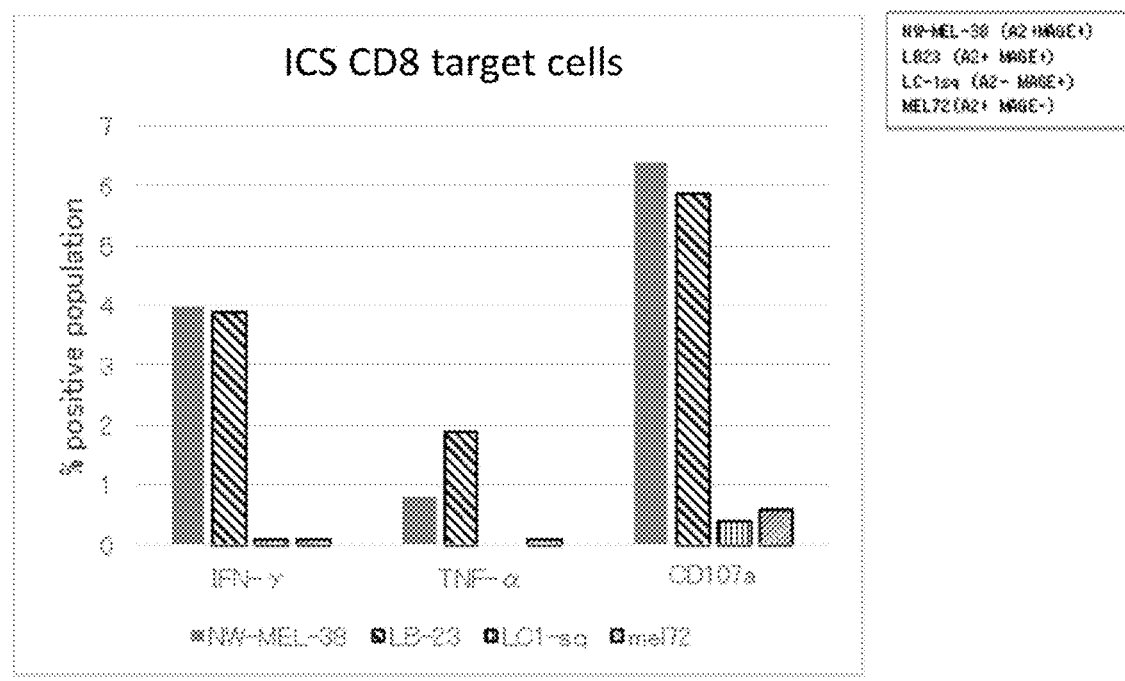
FIG. 15 is a graph showing that T cells transfected with MAGE #17 CAR were activated by co-culture with A2 positive MAGE-A4-positive cells.

As a result, the ratio of CAR-T cell stained with IFN-γ, TNF-α and CD107a was increased in co-culture with T2 cell pulsed with MAGE-A4p230 (FIG. 14). Moreover, the ratio of CAR-T cell stained with IFN-γ, TNF-α and CD107a was increased in co-culture with target cells when co-cultured with A2-positive-MAGE-A4-positive NW-MEL-38 and LB-23 (FIG. 15).

Figure 16:
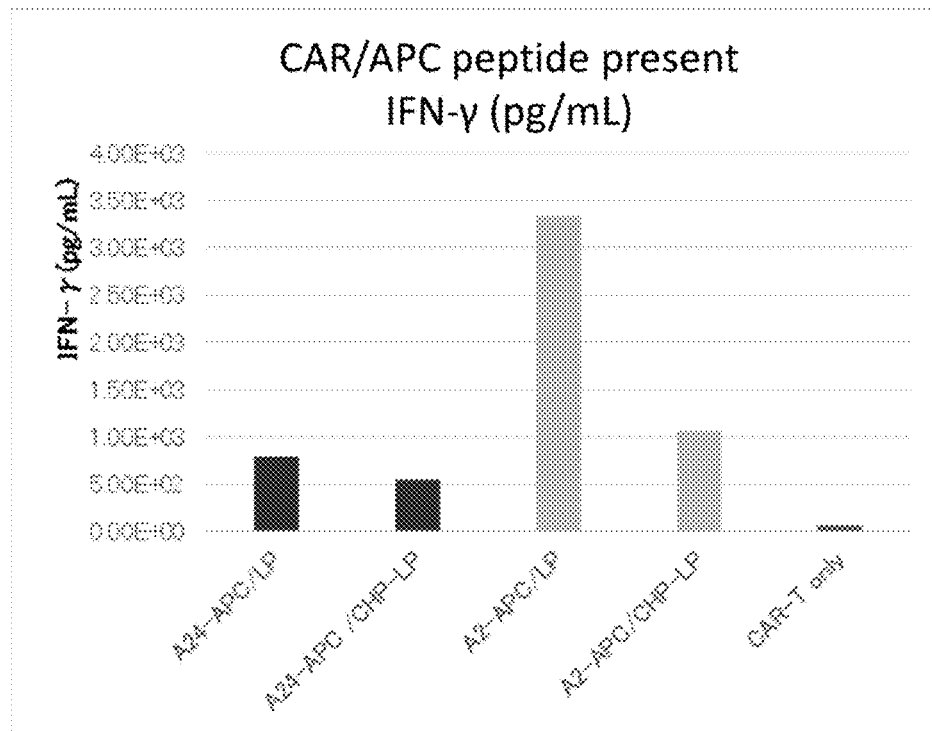
FIG. 16 shows a graph of the results that interferon production by CAR-T was increased when antigen-presenting cells incorporating MAGE-A4 long peptides were co-cultured with CAR-T.

5. The Production of IFN-γ in CAR-T Cells was Increased by Antigen Presentation of Antigen Presenting Cell (APC) that Took MAGE-A4 Long Peptide Antigen PBMCs were separated from healthy human peripheral blood, negative selection was conducted by CD3 magnet beads, and CD3-fractions were used as antigen-presenting cells (APC). A2-APC as APC on which MAGE-A4p230 was presented and A24-APC as APC for negative control were used. MAGE-A4 long peptide and CHP-MAGE-A4 long peptide were added to a final concentration of 10 μM, cultured overnight and co-cultured with CAR-T cells for 24-hours. Gene transfection to CAR-T cells was conducted according to the method of the above section 10 (Gene transfer into cells by retrovirus). As a result, the concentration of IFN-γ in the culture supernatant was increased in co-culture with A2-APC pulsed with MAGE-A4 long peptide (FIG. 16).

MAGE-A4 long peptides were incorporated into APC, MAGE-A4p230 was presented with MHC-class I, IFN-γ production of CAR-T cells which recognized the MAGE-A4p230-MHC-class I complex increased specifically. On the other hand, specific production of IFN-γ was not observed in CHP-MAGEA4 long peptides wrapped in CHP Nanogel as a drug delivery system.

6. CAR-T Cells Wherein MAGE #17 CAR Gene was Transferred Lysed Specifically Target Cancer Cells It was confirmed whether the specific cytotoxic activity of MAGE #17 CAR was observed or not by $^{51}$Cr release assay. When the ratio of CAR-T cells and target cancer cells was E/T ratio (effector/target ratio), cancer cells that took Cr and CAR-T cells were co-cultured for 8 hours with ET ratio was 10:1, 3:1, 1:1, cytotoxicity rate (% lysis) was determined from the radioactivity of $^{51}$Cr in the supernatant. Gene transfer to CAR-T cells was conducted according to the method of the above "10. Gene transfer into cells by retrovirus".

Figure 17:
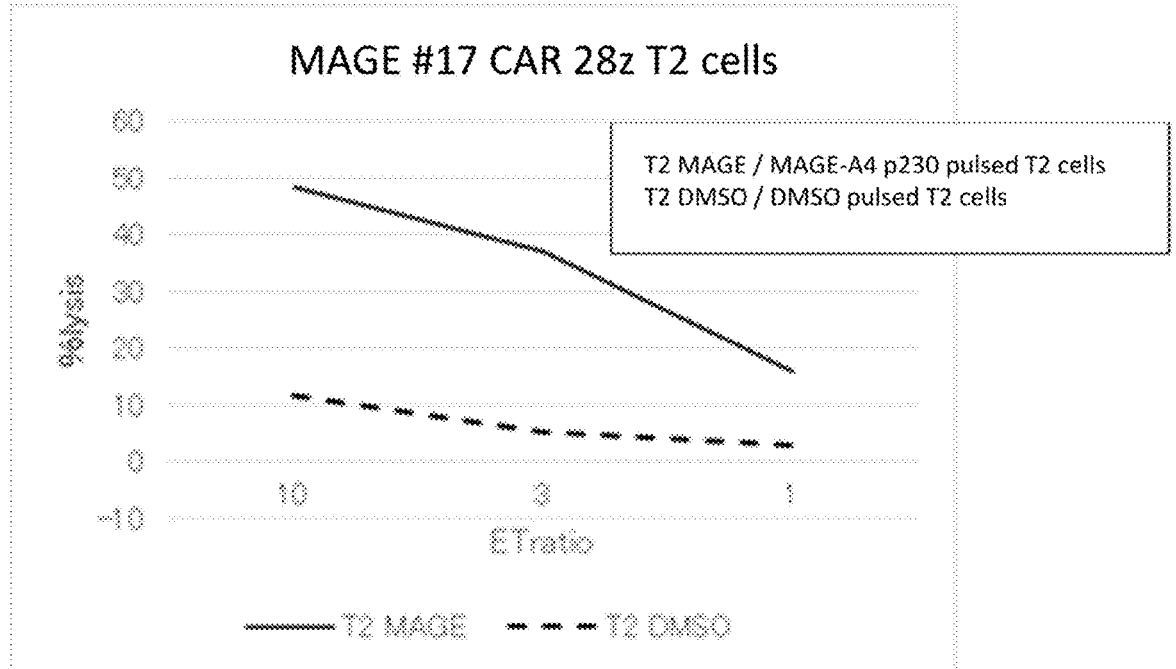
FIG. 17 is a graph showing that T2 cells pulsed with the MAGE-A4 peptide have the MAGE-A4-specific cytotoxic activity.
Figure 18:
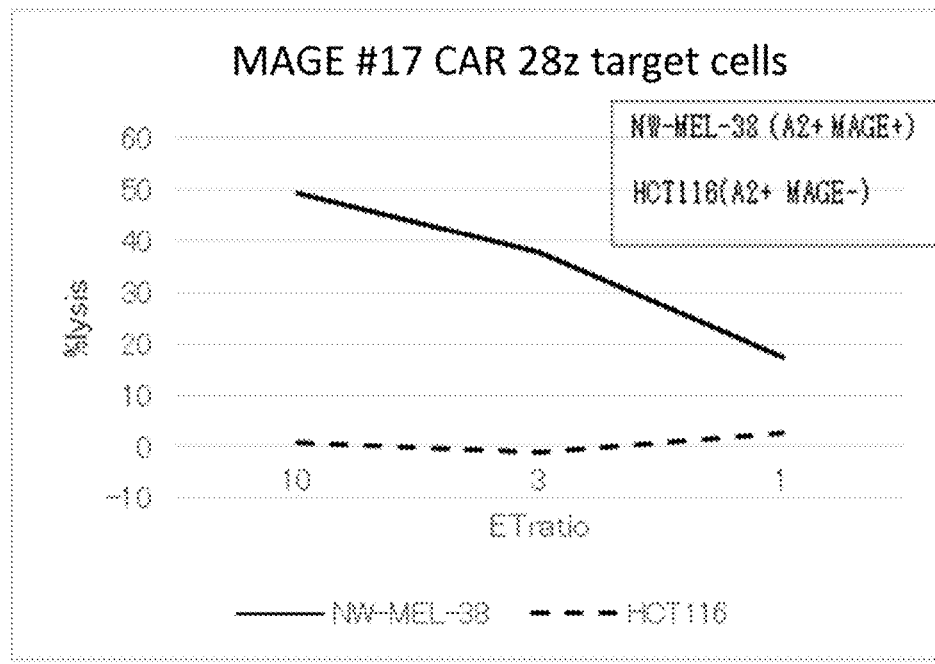
FIG. 18 is a graph showing that the target cells have the specific cytotoxic activity to A2-positive-MAGE-positive cells.

As a result, MAGE-A4 specific cytotoxicity was observed in T2 cells pulsed with MAGE-A4 p230 peptide (FIG. 17). Further, in target cells, specific cytotoxicity was confirmed to NW-MEL-38 cells which were A2-positive-MAGE-A4-positive cells (FIG. 18).

7. Mouse Cancer Therapy Model
(1) Model Using NW-MEL-38 and HCT116

Since the NOG mouse lacks common γ receptors, NK cells do not exist in the NOG mouse. Therefore, engraftment of human cells and human tissue is significantly higher in a NOG mouse than a NOD-SCID mouse, such that human cancer and human tissue can be easily engrafted onto NOG. Further, since differentiation of human T cells is observed after human hematopoietic stem cell transplantation, the NOG mouse model has been expected to serve as a suitable human immune system model. NOG mice have the features containing deletion of T cells and B cells, deletion of natural killer (NK) cells, reduction of dendritic cell functions, decrease of macrophage functions, loss of complement activity, lack of leakage of B cells and T cells associated with aging (leakiness).

Figure 19:
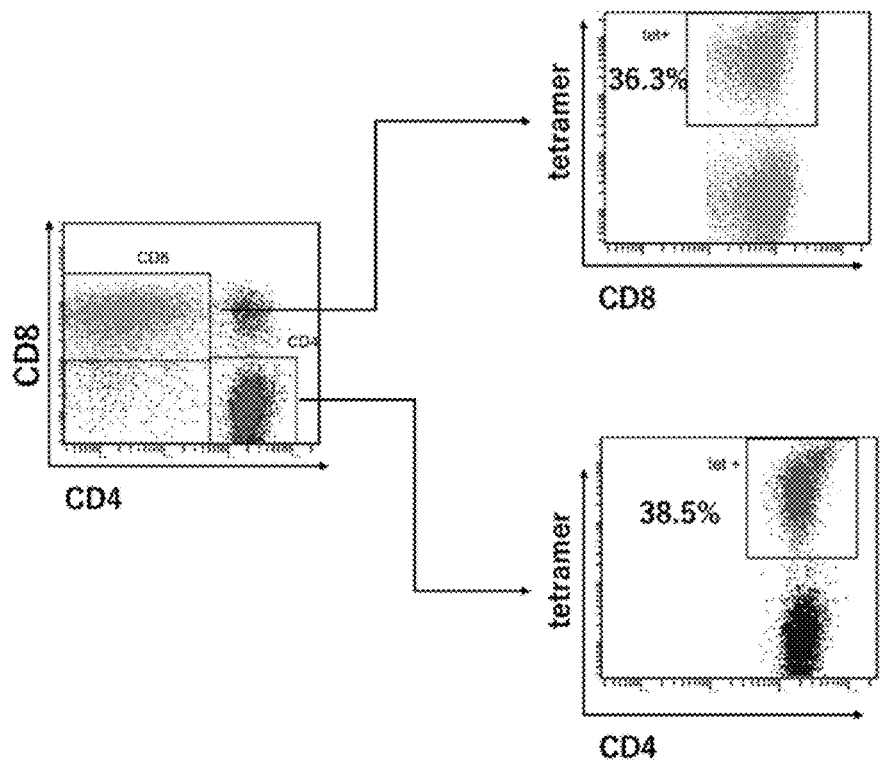
FIG. 19 shows the results of examining the CAR positive rate of infused CAR-T cells by tetramer staining.

For NOG mice, NW-MEL-38 (A2-positive MAGE-A4-positive) at $2.5 \times 10^6$ cells/mouse were injected in the right-side of each mouse, HCT116 (A2-positive MAGE-A4-negative) at $2.5 \times 10^6$ cells/mouse were injected subcutaneously in the left side of each mouse. As a pretreatment, total body irradiation (TBI) with 2.5Gy to NOG mice was conducted 6 days after tumor transplantation. As the TBI reduced lymphocytes in the recipients, transplanted donor lymphocytes would be engrafted easily. On day 7, MAGE #17 CAR-T cells and human lymphocytes were infused via the tail vein at $1 \times 10^7$ cells/animal. Gene transfer to CAR-T cells was conducted according to the method of the above section 10 (Gene transfer into cells by retrovirus). The CAR positive rate was 36.3% by CD8, and was 38.5% by CD4 (FIG. 19).

The experiments were carried out containing CAR-T cells infused group (n=2), human lymphocytes infusion group (CAR untransfected (n=2)), and PBS group (n=2), tumor sizes and body weights were measured every 2-3 days. The measurements were carried out until 42 days after tumor implantation.

Figure 20:
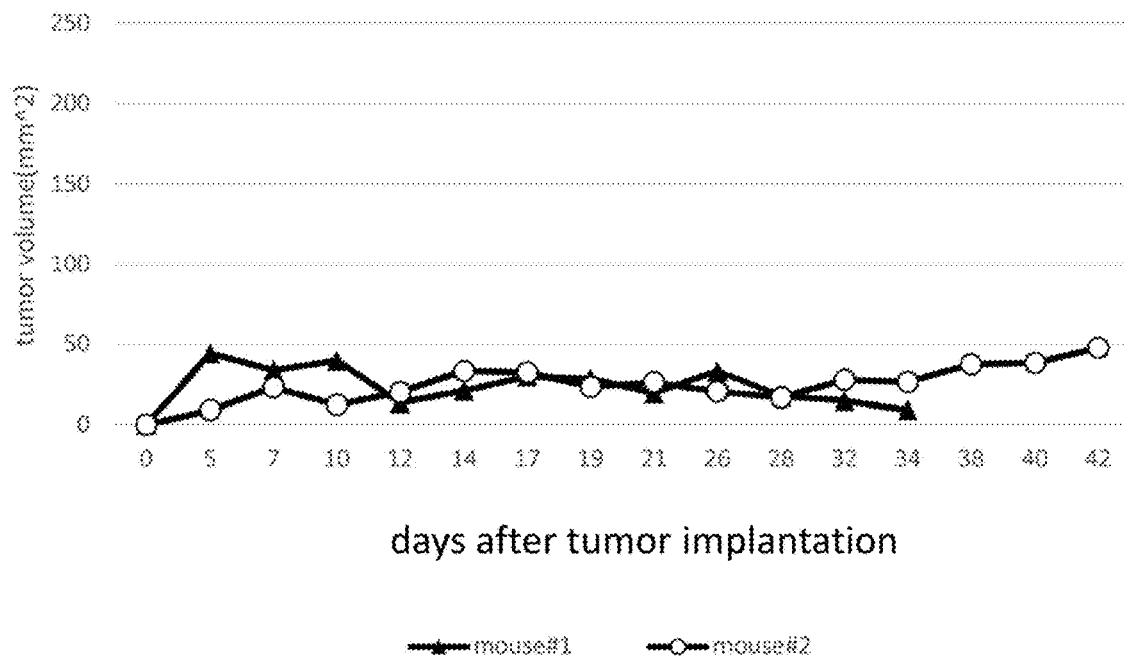
FIG. 20 (A) is a graph showing the results of the effects of CAT-T cells against the A2-positive-MAGE-A4-positive tumor (NW-MEL-38)
Figure 20:
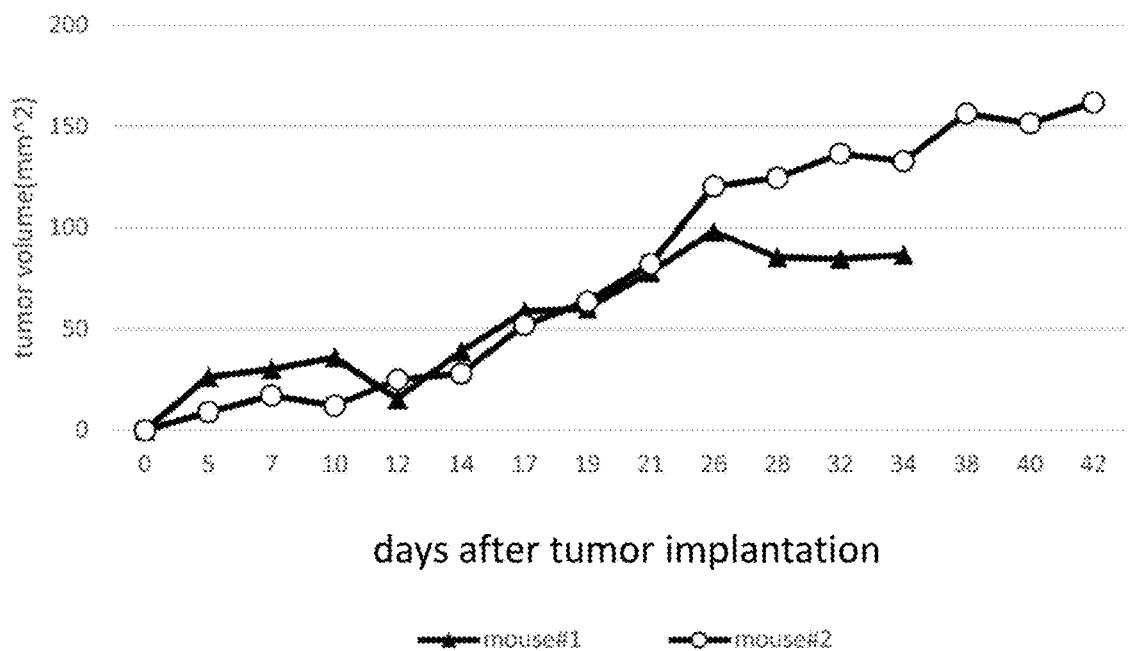

As a result, in CAR-T cells infused group, growth inhibition of NW-MEL-38 (A2 positive MAGE-A4-positive) was observed in mouse #1 and mouse #2. On the other hand, growth inhibition of HCT116 (A2-positive MAGE-A4-negative) was not observed. Mouse #1 died after 34 days from tumor implantation. The cause of death was not a tumor death, but rather an infection (FIG. 20).

(2) Experiments Concerning the Effects of the Differences of the Intracellular Domain (ICD)

Next, the effects of CAR-T cells due to differences in the ICD portion was confirmed. FIG. 21 showed the gene sequence image of CAR zG. In CAR zG, ICD of GITR was used instead that of CD28. GITR is a glucocorticoid-inducible tumor necrosis factor receptor; CAR using this ICR is known that the expression level of cytokines per that of CAR was higher (WO2013051718). In CAR zG, ICD of CD28 in CAR 28z in FIG. 2 was changed ICD of GITR, and the order of CD3 and ICD domains in CAR 28z were changed. Other parts were used with identical sequences of CAR 28z.

NW-MEL-38 (A2-positive MAGE-A4-positive) at $2.5 \times 10^6$ cells/mouse were injected subcutaneously into NOG mice. Three days after tumor implantation, total body irradiation (TBI) with 2.0Gy was conducted as a pre-treatment. On day 4, cells or PBS and human lymphocytes $4 \times 10^6$ cells/mouse to each group A–C (n=4) shown in the following were infused through the tail vein. Gene transfer to CAR-T cells was conducted according to the method of the above section 10 (Gene transfer into cells by retrovirus). PBS in group A, MAGE #17 CAR-T cells in group B (28z), and CAR-T cells (zG) in group C were infused.

The diameter of the tumors and body weight were measured every 2-3 days for groups A to C. The measurements were carried out at 24 days after tumor implantation.

Figure 22:
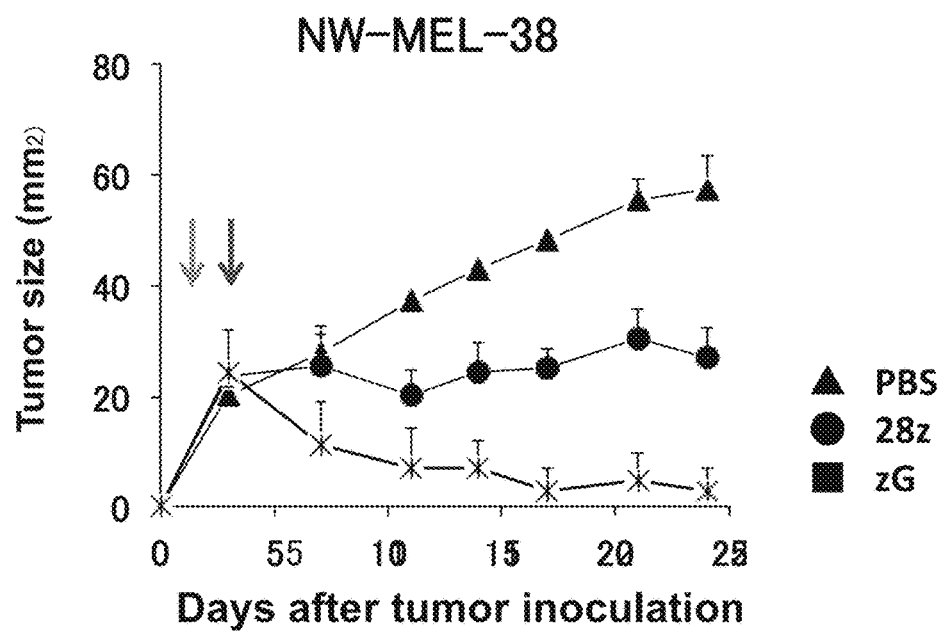
FIGS. 22(A) and 22(B) are graphs showing the results of the effects of CAR-T cells having different intracellular domain (ICD) against A2-positive MAGE-A4-positive tumors (NW-MEL-38). More particularly.
Figure 22:
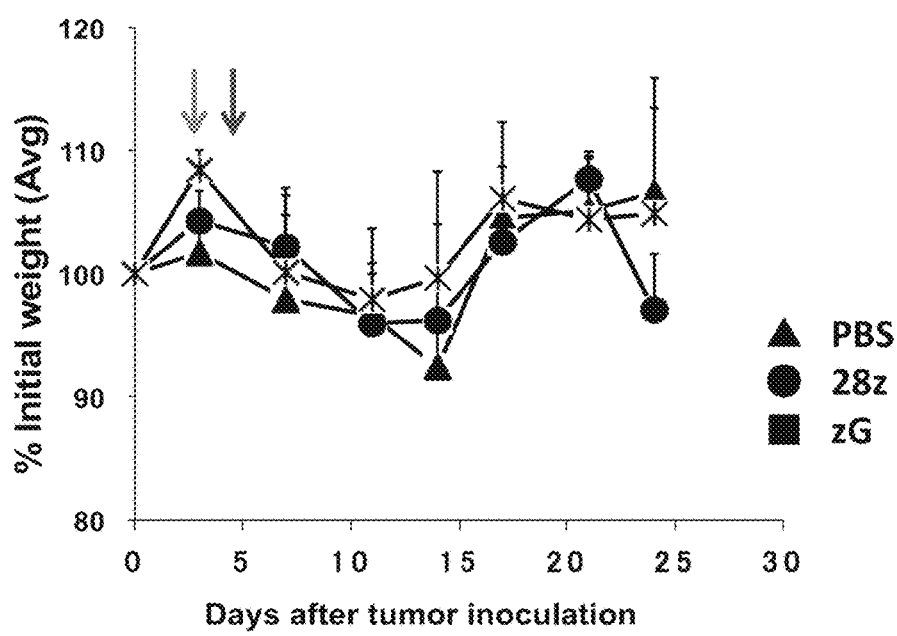

As a result, growth inhibition of NW-MEL-38 (A2-positive MAGE-A4-positive) was observed when CAR-T cells with 28z of ICT or zG of ICT were infused (FIG. 22). In the embodiment, it was found that the same effect was obtained when changing the intracellular domain.

8. Experiments Concerning the Effects of zG Type CAR Introduced CD8-Positive T Cells and 4-1BBz Type CAR Introduced CD8-Positive T Cells (1) Constructing retrovirus vector introduced zG type CAR and 28z type CAR, after preparing retrovirus with packaging cells plat-A, CAR-T cells were produced by infecting the retrovirus into PBMCs. Gene transfer was conducted according to the method of the above section 10

Figure 23:
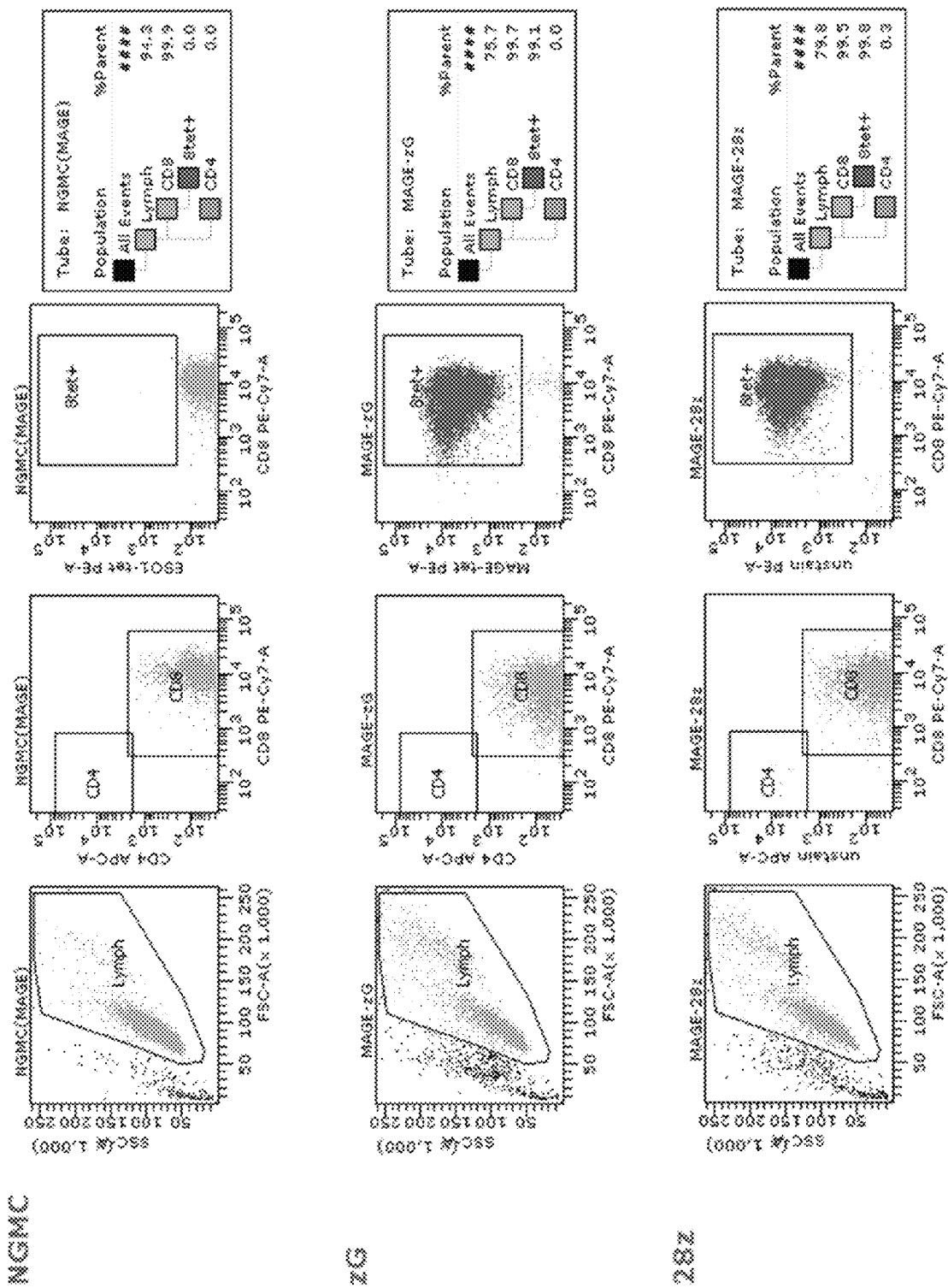
FIG. 23 contains figures showing the results of examining the CAR positive rates of no-CAR introduced CD8-positive T cells (NGMC: control), zG type CAR introduced CD8-positive T cells (zG), and 28z type CAR introduced CD8-positive T cells (28z) by tetramer staining.

(Gene transfer into cells by retrovirus). The expression of CAR was confirmed by tetramer staining. Consequently, the CAR positive rate of zG type CAR-T cells was 99.1% by CD8, and that of 28z type CAR-T cells was 99.8% by CD8 (FIG. 23).

Figure 24:
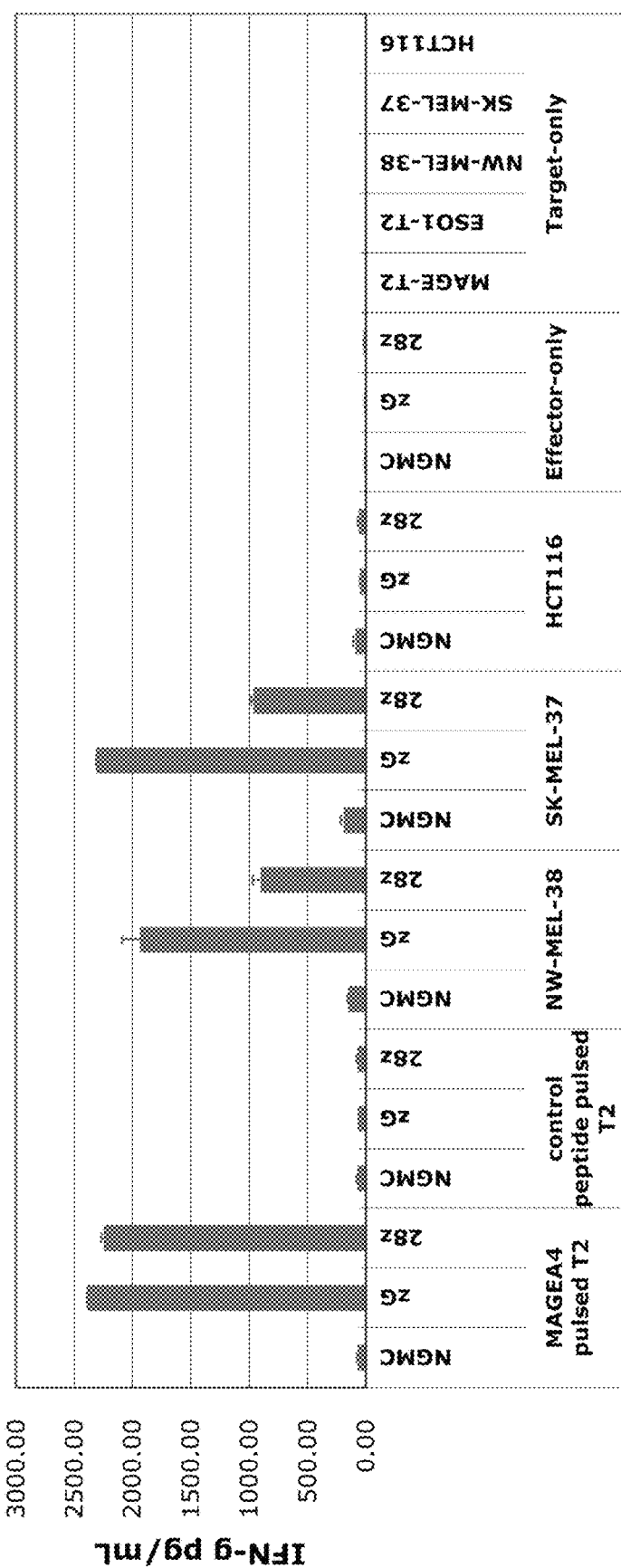
FIG. 24 is a graph which shows the results of examining whether CAR-T cells specifically recognize the target cells and increase the IFNγ production.

(2) Gene-transfected CAR-T cells by retrovirus ($4 \times 10^4$ cells) and peptide-pulsed T2 cells, NW-MEL-38, SK-MEL-37, and HCT116 (respectively $2 \times 10^5$ cells) were co-cultured for 18 hours, INF-γ in the culture supernatant was measured. As shown in FIG. 24, IFN-γ production of was increased specifically in CAR-T cells transfected with zG type CAR and 28z type CAR, in T2 cells pulsed with MAGE-A4 and NW-MEL-38 cells and SK-MEL-37 cells.

A similar assay was conducted using control cells (cells with no gene transfection). IFN-γ production was not observed in A2-positive MAGE-A4 HCT116 as the target cell. IFN-γ production was not observed in effectors only (Effector-only) and target only (Target-only).

Thus, zG type CAR introduced CD8-positive T cells induced INF-γ production in vitro. The data can successfully explain the results obtained in vivo.

Figure 25:
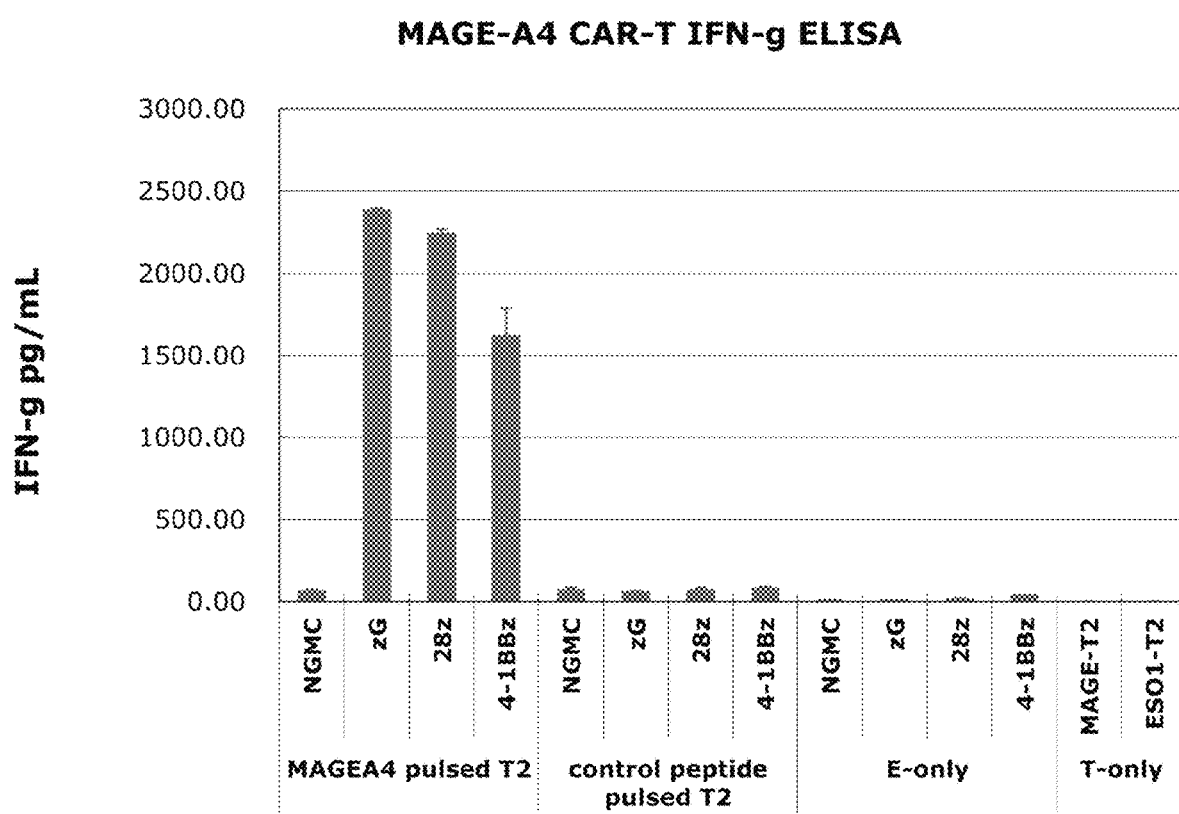
FIG. 25 is a graph which shows the results of examining whether CAR-T cells specifically recognize the target cells and increase the IFNγ production.

(3) Next, similar assays as (1) and (2) were conducted using 4-1BBz type CAR introduced CD8-positive T cells to obtain the characters of the cells. As shown in FIG. 25, in CAR-T cells transfected with 4-1BBz type CAR, IFN-γ production was increased specifically to T2 cells pulsed with the MAGE-A4.

In T2 cells pulsed with control peptide, IFN-γ production was not observed. In effectors only (Effector-only) and target only (Target-only), IFN-γ production was not observed.

Thus, even when ICD was changed to 4-1BBz type, the same effect was observed. The data in vitro can easily explain the results obtained in vivo.

In this way, even when ICD was changed, the same effect as zG type was observed.

Thus, according to these embodiments, an antigen binding protein specifically recognizing the MAGE-A4-derived peptide/HLA-A2 complex, nucleic acids encoding the antigen binding protein, a vector containing the nucleic acids, a chimeric antigen receptor including the antigen binding protein, nucleic acids encoding the chimeric antigen receptor, a vector containing the nucleic acids, a cell expressing the chimeric antigen receptor, and a pharmaceutical composition containing the cells were provided.

The antigen binding protein specifically recognizing the MAGE-A4-derived peptide/HLA-A2 complex can be used in cell therapy and in the field of gene therapy. The present teachings are extremely useful for the detection of tumor cells expressing the MAGE-A4-derived peptide/HLA-A2 complex, for curing tumors, for research and for experiments on tumors. CAR-T cells of the present teachings can provide very effective cancer therapy, since the side effects are very small.

PRIOR ART

Non-Patent Documents

Non-patent Document 1: Brentjens R J, et al: Safety and persistence of adoptively transferred autologous CD19-targeted T cells in patients with relapsed or chemotherapy refractory B-leukemias. Blood 2011, 118:4817-4828.

Non-patent Document 2: Dao T, Yan S, Veomett N, Pankov D, Zhou L, Korontsvit T, et al: Targeting the intracellular WT1 oncogene product with a therapeutic human antibody. Sci Transl Med 2013; 5: 176ra133.

Non-patent Document 3: Van Der Bruggen P, Zhang Y, Chaux P, Stroobant V, Panichelli C, Schultz E S, Chapiro J, Van Den Eynde B J, Brasseur F, Boon T. Tumor-specific shared antigenic peptides recognized by human T cells. Immunological Reviews 2002. Vol. 188: 51-64.

Non-patent Document 4: Duffour M T, Chaux P, Lurquin C, Cornelis G, Boon T, van der Bruggen P. A MAGE-A4 peptide presented by HLA-A2 is recognized by cytolytic T Lymphocytes. Eur. J. Immunol 1999. 29: 3329-3337.

Non-patent Document 5: Muraoka D, Harada N, Hayashi T, Tahara Y, Momose F, Sawada S, Mukai S A, Akiyoshi K, Shiku H. Nanogel-based immunologically stealth vaccine targets macrophages in the medulla of lymph node and induces potent antitumor immunity. ACS Nano. Sep. 23, 2014; 8(09209-18.

Non-patent Document 6: Hillig R C, Coulie P G, Stroobant V, Saenger W, Ziegler A, Huelsmeyer M. High-resolution Structure of HLA-A*0201 in Complex with a Tumour-specific Antigenic Peptide Encoded by the MAGE-A4 Gene. J. Mol. Biol. 2001, 310, 1167-1176.

The invention claimed is:

1. An antigen binding protein comprising:
    a polypeptide comprising the amino acid sequence of VH (heavy chain variable region) of SEQ ID NO: 36 and the amino acid sequence of VL (light chain variable region) of SEQ ID NO: 38;
    wherein:
    between SEQ ID NO: 36 and SEQ ID NO: 38, the antigen binding protein further comprises a polypeptide comprising the amino acid sequence of sc (single chain) of SEQ ID NO: 37: and
    the antigen binding protein recognizes a peptide in a HLA-A2-MAGE-A4 complex having the formula: GVYDGREHTV (SEQ ID NO:1).

2. The antigen binding protein according to claim 1, further comprising a polypeptide comprising the amino acid sequence of SEQ ID NO: 32.

3. The antigen binding protein according to claim 1, wherein the antigen binding protein is a single chain Fv (scFv).

4. A nucleic acid encoding the antigen binding protein according to claim 1.

5. A vector comprising the nucleic acid of claim 4.

6. A chimeric antigen receptor comprising the antigen binding protein according to claim 1 and an intracellular domain of a signal transduction protein.

7. The chimeric antigen receptor of claim 6, wherein the signal transduction protein is CD3zeta (CD3ζ) or GITR.

8. The chimeric antigen receptor of claim 7, further comprising the intracellular domain of CD28 or GITR.

9. A cell expressing the chimeric antigen receptor according to claim 8.

10. A pharmaceutical composition comprising the cell of claim 9 as an active ingredient.

11. A nucleic acid encoding the chimeric antigen receptor according to claim 8.

12. The nucleic acid according to claim 11, wherein:
    the antigen binding protein includes a polypeptide comprising the amino acid sequence of SEQ ID NO: 32; and
    the antigen binding protein is a single chain Fv (scFv).

13. A vector comprising the nucleic acid of claim 12.

14. A nucleic acid encoding the chimeric antigen receptor according to claim 6.

15. A vector comprising the nucleic acid of claim 14.

16. A cell expressing the chimeric antigen receptor according to claim 6.

17. A pharmaceutical composition comprising the cell of claim 16 as an active ingredient.

18. A method of treating a patient having a hematopoietic tumor that is MAGE-A4-positive and HLA-A2 positive or a patient having a solid cancer that is MAGE-A4-positive and HLA-A2 positive, comprising:
    administering a therapeutically effective amount of the pharmaceutical composition of claim 17 to the patient.

19. The cell according to claim 16, wherein the antigen binding protein is located outside of the cell and the intracellular domain of the signal transduction protein is located inside the cell.

20. The antigen binding protein according to claim 1, wherein:
    the antigen binding protein includes a polypeptide comprising the amino acid sequence of SEQ ID NO: 32; and
    the antigen binding protein is a single chain Fv (scFv).

* * * * *